US006673560B1

(12) United States Patent
Sharpe et al.

(10) Patent No.: US 6,673,560 B1
(45) Date of Patent: Jan. 6, 2004

(54) MEASUREMENT OF HYDRIDE USING CHEMILUMINESCENT ACRIDINIUM COMPOUNDS AND APPLICATIONS THEREOF

(75) Inventors: David Sharpe, Foxborough, MA (US); Anand Natrajan, Manchester, NH (US); Qingping Jiang, Northborough, MA (US); George Parsons, Arlington, MA (US); Say-Jong Law, Westwood, MA (US)

(73) Assignee: Bayer Corporation, Tarrytown, NY (US)

( * ) Notice: Subject to any disclaimer, the term of this patent is extended or adjusted under 35 U.S.C. 154(b) by 0 days.

(21) Appl. No.: 09/448,522

(22) Filed: Nov. 23, 1999

Related U.S. Application Data
(60) Provisional application No. 60/109,823, filed on Nov. 25, 1998.

(51) Int. Cl.[7] ............... G01N 33/536; G01N 33/573; G01N 33/98; G01N 21/76
(52) U.S. Cl. ............... 435/7.7; 435/6; 435/7.4; 435/7.9; 435/7.91; 435/7.92; 435/7.94; 435/26; 436/132; 436/172; 436/536; 436/800; 436/815
(58) Field of Search ............... 436/501, 536, 436/544, 546, 548, 800, 172, 543, 132, 815; 435/6, 28, 7.1, 968, 7.92, 7.94, 7.4, 7.7, 7.9, 7.91, 26; 530/389.8; 424/94.1, 94.2, 94.4

(56) References Cited
U.S. PATENT DOCUMENTS
4,745,181 A   5/1988   Law et al.
(List continued on next page.)

FOREIGN PATENT DOCUMENTS
EP   0 324 202 A1   7/1989
(List continued on next page.)

OTHER PUBLICATIONS
Sato, N. "Synthesis and Properties of New Luminescent 10–Carboxymethylacridinium Derivatives" *Tetrahedron Letters*, vol. 37, No. 47, (1996) pp. 8519–8522.

(List continued on next page.)

*Primary Examiner*—Mary E. Ceperley
(74) *Attorney, Agent, or Firm*—Weingarten, Schurgin, Gagnebin & Lebovici LLP

(57) ABSTRACT

The present invention discloses a method for the measurement of hydride using a chemiluminescent compound. The preferred chemiluminescent molecule is an acridinium compound. The source of hydride for the reduction of acridinium compound may be of chemical or biochemical origin, or the result of enzymatic catalysis. The chemical source of hydride, for example, might be metal hydrides, such as $NaBH_4$. A biochemical source of hydride might be that derived from NADH, or NADPH, while an enzymatic source would be the class of oxidoreductases termed dehydrogenases which convert NADH or NADPH from NAD or NADP.

There are numerous potential applications for acridinium compounds as chemiluminescent indicators of hydride. Any applied tests or diagnostic assays, in which hydride is either present at the onset of or generated through the course of a reaction, would benefit from the present invention. Such tests, which could encompass many different formats as discussed below in detail, may involve the quantitation or detection of metal hydrides, or enzyme cofactors such as NADH, NADPH, $FMNH_2$, or $FADH_2$. Of particular importance, are those diagnostic assays which might use dehydrogenases as reagents, indicators, diagnostic markers or as labels. Ethanol, for example, might be detected with acridinium ester chemiluminescence through the reaction of alcohol dehydrogenase on ethanol, said reaction producing NADH. As a label, dehydrogenase might be used in an ELISA for the detection of a specific analyte with acridinium ester providing the signaling response. Nucleic acid assays using dehydrogenase as a label are also envisioned. Assays for the detection of clinically relevant dehydrogenases such as elevated glutamate dehydrogenase as an indicator of hepatocellular damage might also be developed.

24 Claims, 11 Drawing Sheets

U.S. PATENT DOCUMENTS

| | | | |
|---|---|---|---|
| 4,918,192 A | | 4/1990 | Law et al. |
| 4,950,613 A | * | 8/1990 | Arnold, Jr. et al. |
| 5,110,932 A | | 5/1992 | Law et al. |
| 5,227,489 A | | 7/1993 | Law et al. |
| 5,241,070 A | | 8/1993 | Law et al. |
| 5,384,265 A | * | 1/1995 | Kidwell et al. ............. 136/525 |
| 5,395,752 A | | 3/1995 | Law et al. |
| 5,449,556 A | | 9/1995 | Law et al. |
| 5,468,646 A | | 11/1995 | Mattingly et al. |
| 5,538,901 A | | 7/1996 | Law et al. |
| 5,543,524 A | | 8/1996 | Mattingly et al. |
| 5,545,739 A | | 8/1996 | Mattingly et al. |
| 5,565,570 A | | 10/1996 | Mattingly et al. |
| 5,595,875 A | | 1/1997 | Law et al. |
| 5,624,813 A | * | 4/1997 | Mahant ...................... 435/28 |
| 5,656,426 A | | 8/1997 | Law et al. |
| 5,663,074 A | | 9/1997 | Law |
| 5,669,819 A | | 9/1997 | Mattingly et al. |
| 5,702,887 A | | 12/1997 | Law et al. |
| 5,879,894 A | | 3/1999 | Law et al. |
| 6,127,140 A | * | 10/2000 | Vidakovic et al. |
| 6,165,800 A | * | 12/2000 | Jiang et al. ................. 436/546 |

FOREIGN PATENT DOCUMENTS

| | | |
|---|---|---|
| EP | 0 609 885 A1 | 8/1994 |
| WO | WO 95/29255 | 11/1995 |
| WO | WO 98/54574 | 12/1998 |
| WO | WO 00/09487 | 2/2000 |

OTHER PUBLICATIONS

Akhavan–Tafti, H., et al. "Characterization of Acridancarboxylic Acid Derivatives as Chemiluminescent Peroxidase Substrates" *Journal of Organic Chemistry,* vol. 64, No. 4, (1998) pp. 930–937.

Littig, J.S. et al, "Flow Injection Chemiluminescence Study of Acridinium Ester Stability and Kinetics of Decomposition" *Journal of Bioluminescence and Chemiluminescene,* vol. 8 (1993) pp. 25–31.

Hammond, P. W. et al., "Nucleophilic Addition to the 9 Position of 9–Phenylcarboxylate–10–Met Hylacridinium Protects Against Hydrolysis of the Ester" *Journal of Bioluminescence and Chemiluminescence,* vol. 6, No. 1 (1991) pp. 35–43.

Czerlinski, G.H., et al. "Coupling of Redox Indicator Dyes into an Enzymatic Reaction Cycle" *Journal of Biochemical and Biophysical Methods,* vol. 15 (1988) pp. 241–248.

M. Kawaguchi et al; *Proceedings of 9th International Symposium 1996;* ed. Hastings, et al. 1997, pp. 481–484.

M. Czerlinski, et al., 15 *Journal of Biochemical and Biophysical Methods,* (1998), pp. 241–247.

Rodbard, MD, *Mathematics and Statistics of Ligand Assays: An Illustrated Guide,* Langan, J., Clapp, J. (eds.), Ligand Analysis (1981), Masson Publishing USA, Inc., NY.

Nakamura, S., et al., *Clinica Chimica Acta,* 101 (1980), pp 321–326.

Bird, C..L., *Chem. Soc. Rev.,* 10, (1981), pp. 49–82.

Van Lente, F., et al., *Enzyme–immunoassay:* (1980) CRC Press, Inc. Boca Raton, Maggio, E. (ed.): pp. 135–153.

Nix, B., *The Immunoassay Handbook*; (1994) Stockton Press, Inc., New York; pp 117–123.

Akhavan–Tafti, H., et al., *Chemiluminescent Detection of Oxidase Enzymes by Peroxidase–mediated Oxidation of Acridan Compounds, Bioluminescence and Chemiluminescence* (1996), pp. 501–504.

Akhavan–Tafti, H., et al., LumigenTM APS: *New Substrates for the Chemiluminescent detection of Phosphatase Enzymes, Bioluminescence and Chemiluminescence* (1996), pp. 311–314.

Ottaway, J.M., 51 *International Serier of Monographs on Analytical Chemistry,* Belcher, R. and Frieser, H., eds.; pp. 469–529.

Cook, D., et al., 39/6 *Clin. Chem.* (1993), pp. 965–971.

Johannsson, Al, et al., 87, *Jour. Immunol. Meth.* (1986), pp. 7–11.

Schneider, R., "*Recent Advances in Enzyme Immunoassay*", Ligand Assay, Langan, J. and Clapp, J. (eds.), Masson Publishing USA, Inc. (1981); pp. 151–181.

* cited by examiner

| NADH eq. | % Residual Chemiluminescent Activity |
|---|---|
| 0 | 100 |
| 0.1 | 94 |
| 0.2 | 85 |
| 0.4 | 46 |
| 0.6 | 38 |
| 0.8 | 30 |
| 1.0 | 17 |

W = N, CH
Long-wavelength Emission

Short-wavelength emission

AE-Quencher conjugate
Lower quantum yield
due to quenching effect

AE-Modified Quencher conjugate
Higher quantum yield due to
reduced quenching effect E.T. = Energy Transfer Rhodamine-AE conjugate emits light at λmax 628 nm due to efficient energy transfer from AE to rhodamine E.T. = Energy Transfer Reduced Rhodamine-AE conjugate is expected to emit light at AE's wavelength because reduced Rhodamine is no longer fluorescent.

Homogeneous Immunoassay Using Acridinium Compound as Hydride Indicator

AC = acridinium compound; ACH = reduced acridinium compound

Heterogeneous Immunoassay Uing Acridinium Compound as Hydride Indicator

**Chemiluminometric *Emit*® Theophylline Assay using NSP-DMAE$_4$-BSA as a Hydride Indicator**

Chemiluminometric *Emit*® Valproate Assay using NSP-DMAE$_4$-BSA as a Hydride Indicator Chemiluminometric *Emit*® Quinidine Assay using NSP-DMAE$_4$-BSA as a Hydride Indicator

| Referenced vs. Determined Analyte Concentration for Controls | | | | | | |
|---|---|---|---|---|---|---|
| | Theophylline Concentration (µM) | | | Valproate Concentration (µM) | | |
| | Controls | | | | | |
| Referenced | 1 | 2 | 3 | A | B | C |
| Ciba-Corning ACS:180® | 21-33 | 60-86 | 119-189 | 104-173 | 381-451 | 589-659 |
| Syva Emit 2000® | 27-41 | 75-111 | 159-237 | - | - | - |
| Determined | 15.4 | 42.3 | 133 | 116 | 337 | 567 |

MEASUREMENT OF HYDRIDE USING CHEMILUMINESCENT ACRIDINIUM COMPOUNDS AND APPLICATIONS THEREOF

CROSS REFERENCE TO RELATED APPLICATIONS

U.S. Provisional Application No. 60/109,823 filed Nov. 25, 1998 entitled: Modulation of Chemiluminescent Acridinium Compounds by Hydrides or Hydride Generating Systems and Applications Thereof.

BACKGROUND OF THE INVENTION

Acridinium esters (AE) have provided for an extremely sensitive method of detection and have been used extensively as chemiluminescent labels in both immuno- and nucleic acid assays. Hydrolytically stable, Polysubstituted Aryl Acridinium Esters (PAAE) have proven useful as analytical labels (U.S. Pat. Nos. 4,745,181; 4,918,192; and 5,110,932) with a variety of linkages (U.S. Pat. Nos. 5,241,070; 5,538,901; and 5,663,074) and were the first chemiluminescent, acridinium compounds to satisfy the stringent requirements of commercial ligand binding assays. The utility of PAAE was further enhanced with the advent of Functionalized Hydrophilic PAAE (U.S. Pat. No. 5,656,426) which increased the quantum yield of PAAE and enhanced the performance of PAAE-labeled binding partners in terms of the observed signal to noise ratios and the sensitivities of various binding assays. Additionally, introduction of ionizable groups at the phenoxy moiety produced another sub-class of hydrophilic PAAE (U.S. Pat. Nos. 5,227,489; 5,449,556; and 5,595,875).

M. Kawaguichi, et al. (Bioluminescence and Chemiluminescence, Proceedings of $9^{th}$ International Symposium 1996, Ed. Hastings, Kricka and Stanley, John Wiley μSons, 1997, pp. 480–484) have described stabilized phenyl acridinium esters for chemiluminescent immunoassays. AE derivatives with additional methyl substitutions at C-1, which are optional at C-3 of the acridinium nucleus with matching mono- or di-methyl substitutions at the ortho-positions of the phenoxy moiety, were shown to have excellent stability in aqueous solution.

EP 0324,202 A1 and subsequently EP 0609,885 A1 both describe acridinium esters with functional groups substituted at the nitrogen atom of the acridinium nucleus. The latter application further describes alternate substituents such as the biphenyl or naphthyl moieties as possible replacements for the phenyl group.

Mattingly, et al. (U.S. Pat. Nos. 5,468,646 and 5,543,524) describe chemiluminescent acridinium salts, and their applications in immunoassays. These acridinium salts belong to another class of compounds termed acridinium sulfonylamides (or N-sulfonylacridinium carboxamides). The acridinium sulfonylamides (AS) have aqueous stabilities which are comparable with PAAE. Mattingly, et al. further describe and claim the analogous chemiluminescent phenanthridinium salts, and their applications in immunoassays, in U.S. Pat. Nos. 5,545,739; 5,565,570; and 5,669,819. Additionally, in these patents a general structure of acridinium sulfonylamides is described showing possible substitutents of a Markush group at the acridinium nucleus.

Conventional acridinium compounds, such as those described in the aforementioned patents and literature, emit light with maxima at about 428 nm upon reaction with hydrogen peroxide in strong alkaline solution. Acridinium compounds which emit light of wavelength maxima >500 nm have also been described in the prior arts. U.S. Pat. Nos. 5,395,752; 5,702,887 and 5,879,894 describe novel, long-emission acridinium esters (LEAE), where a fused, benzacridinium system is employed to extend the wavelength of emission of the acridinium ester. In the copending PCT application PCT/IB98/00831 Jiang et al. have further extended the PAAE emission maxima well into the region of 600–700 nm by utilizing the principle of energy transfer. This entailed the covalent coupling of luminophores to acridinium ester. When the chemiluminescent reactions of these conjugates were initiated by treatment with alkaline peroxide, light emission was observed at long wavelengths where the wavelength maxima depended upon the structure of the luminophore. In the more recent copending PCT application PCT/US99/18076, Natrajan et al. describe novel acridinium compounds that have intrinsic emission maxima close to or in the near infrared region (>590 nm). The structural requirements for such long wavelength-emitting acridinium compounds are disclosed.

N-Alkylacridan esters obtained from the reduction of acridinium esters have been used as enzyme substrate indicators for the determination of phosphatases and oxidases and their substrates or products. N-alkylacridan phosphate esters have been engineered as substrates for the direct detection of minute concentrations of alkaline phosphatase (Akhavan-Tafti, H et al. "Lumagen™ APS: New Substrates for the Chemiluminescent Detection of Phosphatase Enzymes"; Proc. 9th. Internat'l. Symp. Bioluminescence and Chemiluminescence; (1996); Hastings, J. W.; Kricka, L. J.; Stanley; P. E., (Eds.); John Wiley & Sons, Inc., New York, N.Y.; pp. 311–314). Similarly, N-alkylacridancarboxylate esters have been applied as oxidizable indicators for horseradish peroxidase, where the chemiluminescence from the oxidized acridinium ester product was used to quantify either horseradish peroxidase or oxidases and their substrates in coupled enzymatic reactions (Akhavan-Tafti, H et al.; Chemiluminescent Detection of Oxidase Enzymes by Peroxidase-mediated Oxidation of Acridan Compounds; Proc. 9th. Internat'l. Symp. Bioluminescence and Chemiluminescence; (1996); Hastings, J. W.; Kricka, L. J.; Stanley; P. E., (Eds.); John Wiley μSons, Inc., New York, N.Y.; pp. 501–504).

Luminols along with peroxidase have been used as chemiluminescent detectors of hydrogen peroxide generated from dehydrogenase and its cofactors (WO 95/29255).

Various classes of chromogenic, hydride-reducible indicators have been described (Ottaway, J. M.; Oxidation-Reduction Indicators; Internat'l Ser. Monographs Anal. Chem.; (1968); Belcher, R.; Frieser, H., (Eds.); Plenum; pp. 469–529) (Bird, C. L.; Kuhn, A. T.; Electrochemistry of the Viologens; Chem. Soc. Rev.; (1981), 10, pp. 49–82). Several of these, including the oxidized salts of phenazines, phenoxazines and phenothiazines, have been used as chromogenic indicators of hydride from the reduced nicotinamide cofactors (dihydronicotinamide adenine dinucleotide, NADH, and dihydronicotinamide adenine dinucleotide phosphate, NADPH) and the reduced flavin cofactors (dihydroflavin mononucleotide, $FMNH_2$ and dihydroflavin adenine dinucleotide, $FADH_2$) generated by the enzymatic activity of dehydrogenases (Czerlinski, G. H., et al., "Coupling of Redox Indicator Dyes into an Enzymatic Reaction Cycle", J. Biochem. Biophys. Methods, (1988) 15, pp. 241–248) (Nakamura, S., et al., "Use of 1-Methoxy-5-methylphenaziniummethylsulfate in the Assay of Some Enzymes of Diagnostic Importance", Clin. Chim. Acta, (1980), 101, p. 321).

BRIEF SUMMARY OF THE INVENTION

The present invention discloses a method for the measurement of hydride using a chemiluminescent compound.

The preferred chemiluminescent molecule is an acridinium compound. The source of hydride for the reduction of acridinium compound may be of chemical or biochemical origin, or the result of enzymatic catalysis. The chemical source of hydride, for example, might be metal hydrides, such as $NaBH_4$. A biochemical source of hydride might be that derived from NADH, NADPH, $FMNH_2$ or $FADH_2$, while an enzymatic source would be the class of oxidoreductases termed dehydrogenases which convert in redox reactions NADH, NADPH, $FMNH_2$ or $FADH_2$ from NAD, NADP, FMN or FAD.

There are numerous potential applications for acridinium compounds as chemiluminescent indicators of hydride. Any applied tests or diagnostic assays, in which hydride is either present at the onset of or generated through the course of a reaction, would benefit from the present invention. Such tests, which could encompass many different formats, as discussed below in detail, may involve the quantitation or detection of metal hydrides, or enzyme cofactors such as NADH, NADPH, $FMNH_2$, or $FADH_2$. Of particular importance, are those diagnostic assays which might use dehydrogenases as reagents, indicators, diagnostic markers or as labels. Ethanol, for example, might be detected with acridinium ester chemiluminescence through the reaction of alcohol dehydrogenase on ethanol, said reaction producing NADH. As a label, dehydrogenase might be used in an ELISA for the detection of a specific analyte with acridinium ester providing the signaling response. Nucleic acid assays using dehydrogenase as a label are also envisioned. Assays for the detection of clinically relevant dehydrogenases such as elevated glutamate dehydrogenase as an indicator of hepatocellular damage might also be developed.

DETAILED DESCRIPTION OF THE INVENTION

Central to the present invention is our discovery that the chemiluminescent activity of an acridinium compound can be modulated (increased or decreased) by hydride. Although the examples discussed herein result in a decrease in chemiluminescent activity, several mechanisms are contemplated wherein one will see an increase in chemiluminescent activity. For example, in Section B2 and part of Section B3, below, chemiluminescence can be increased when the detector is sensitive to a selective range of emission wavelength. If the reaction results in a shift of the emission to a wavelength where a detector is more sensitive, increased chemiluminescence will be observed. In the other part of Section B3, below, an increase is observed because the moiety causing quenching is reduced and inactivated by the hydride.

A. Novel Chemiluminescent Indicators of Hydride

Figures 1, 2:
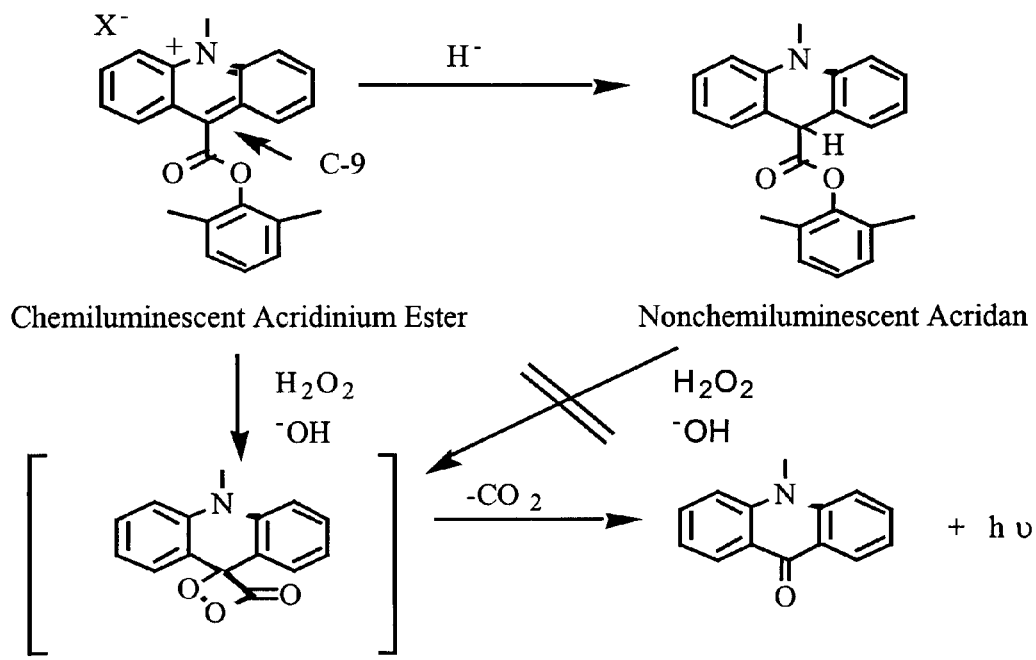
FIG. 1 is the reaction showing the addition of hydride to C-9 of the acridinium nucleus.
FIG. 2 shows reduction of 2',6'-Dimethylphenyl-10-Methyl Acridinium-9-Carboxylate with NADH in DMF/0.1 M phosphate pH 7.4 at room temperature for 10 minutes.

We have discovered that reduction of acridinium ester with hydride suppresses the chemiluminescent activity of the acridinium ester. The reduction in chemiluminescent activity is the result of the addition of hydride to C-9 of the acridinium nucleus (see FIG. 1). The product, which is the acridan, is unable to participate in the light-generating reaction with alkaline hydrogen peroxide. Other chemiluminescent acridinium compounds or analogs (e.g. benzacridinium, phenanthridinium, quinolinium compounds or isomers) and their derivatives, as well as chemiluminescent compounds such as lucigenin and its derivatives, share the same or similar mechanism of hydride attack to the electron-deficient acridinium nucleus to form the reduced acridans.

Our initial studies focused on the reduction of 2',6'-dimethylphenyl-10-methyl acridinium-9-carboxylate (DMAE-Φ) with the chemical reductant sodium borohydride in methanol solvent. Chromatographic analysis (HPLC) of this reduction reaction revealed clean conversion to the corresponding N-methylacridan, correlating with a drop in chemiluminescent activity when the reaction mixture was treated with alkaline peroxide. A similar result was also observed when the hydride donor NADH was employed to reduce the acridinium ester. Chromatographic analysis of this reaction too revealed clean formation of the acridan with a concomitant loss of chemiluminescent activity. The extent of this decrease was found to depend upon the concentration of NADH. As shown in the table in FIG. 2, increasing quantities of NADH were accompanied by a corresponding decrease in the chemiluminescent activity of the reaction mixture. The reduction reaction was complete in less than 10 minutes.

Measurement of hydride generated in enzymatic systems has been used in the prior art to devise sensitive assays. For example, Cook et al. in Clin. Chem. 1993, 39/6, 965–971 describe an enzyme amplification system to detect human proinsulin in human plasma. This assay involves using a alkaline phosphatase as the primary label which is used to dephosphorylate $NADP^+$ to $NAD^+$. The latter compound is then employed as a cofactor in a redox cycle using the enzymes alcohol dehydrogenase and diaphorase. While the former enzyme utilizes $NAD^+$ to oxidize ethanol to acetaldehyde with generation of NADH, the latter enzyme diaphorase utilizes the NADH for the reduction of a tetrazolium dye to produce a colored formazan dye. Using this system, Cook et al. were able to detect 1 zeptomole of alkaline phosphatase and 0.017 pmol/L of human proinsulin. The same system was employed by Johannsson et al. (J. Immunol. Meth. 1986, 87, 7–11) to devise a highly sensitive assay for TSH (sensitivity of 0.0013 μIU/L). Both the above assays use a colored dye as an indicator. Since chemiluminescent indicators such as acridinium esters are much more sensitive, measuring hydride using these compounds is likely to produce more sensitive assays. We envisage other interesting and useful applications of our finding which we will elaborate in greater detail later.

The reduction of 2',6'-dimethylphenyl-10-methyl acridinium ester with NADH involves addition of hydride to C-9 to generate the non-chemiluminescent acridan. It is evident that acridinium compounds and analogs with widely different structural modifications, but containing the same core acridinium nucleus or the analogous benzacridinium, phenanthridinium, or quinolinium nucleus will be amenable to this transformation. Such compounds can be generalized with the structure(s), which have been described in all the prior arts references incorporated herein in the background section at the beginning of this disclosure. These structures include not only blue-emitting (about 420–490 nm), but also green (about 490–570 nm), yellow (about 570–580 nm), orange (about 580–595 nm) and red (about 595–780 nm)-emitting acridinium compounds and said analogs.

Figure 3:
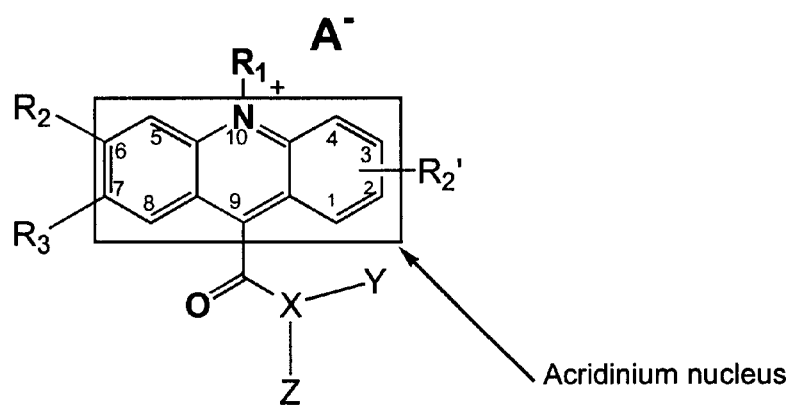
FIG. 3 shows the general structure of the main acridinium compounds useful as the chemiluminescent indicators of the present invention.

For further illustration, the general structure of the main acridinium compounds useful as the chemiluminescent indicators of the present invention can be schematically represented as shown in FIG. 3, wherein $R_1$, is an alkyl, alkenyl, alkynyl or aralkyl containing optionally up to 20 heteroatoms; preferably $R_1$ is methyl or sulfoalkyl group.

Figure 4:
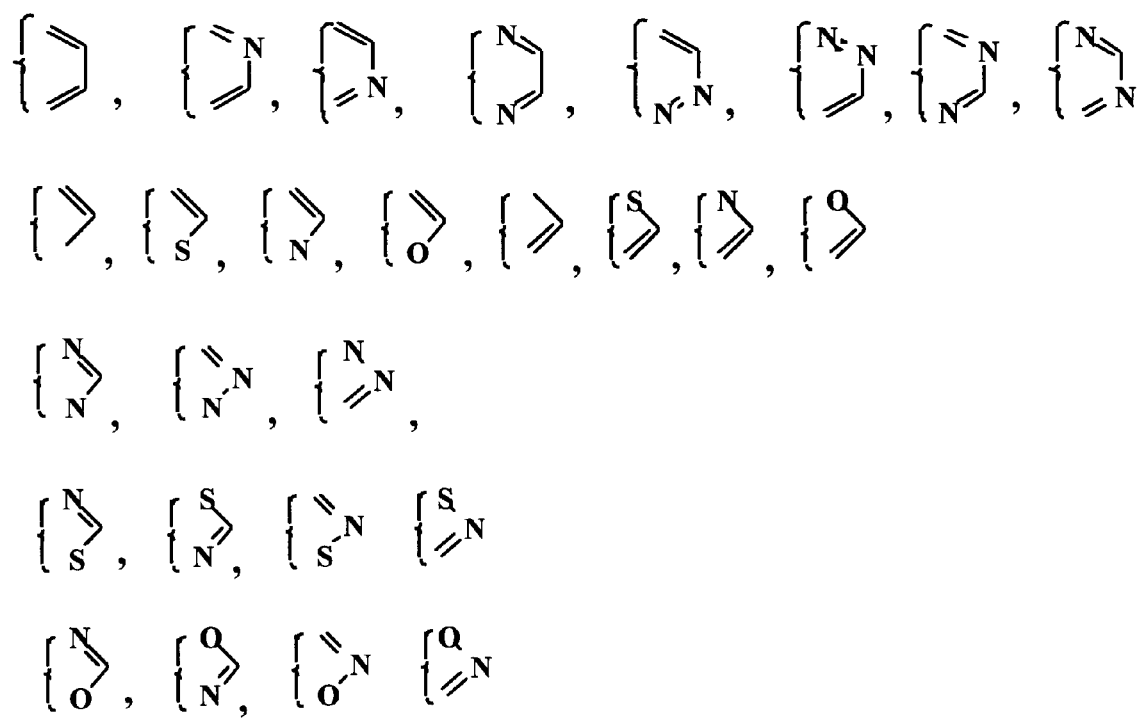
FIG. 4 shows the additional structures that can be linked to $R_2$ and $R_3$ to form an additional ring.

$R_2$, $R_2'$, and $R_3$, are identical or different, selected from hydrogen, —R, substituted or unsubstituted aryl (ArR or Ar), halide, amino, hydroxyl, nitro, sulfonate, —CN, —COOH, —SCN, —OR, —SR, —SSR, —C(O)R, —C(O)OR, —C(O)NHR, or —NHC(O)R;

Throughout this application, R is selected from the group consisting of alkyl, alkenyl, alkynyl, aryl, and aralkyl containing optionally up to 20 heteroatoms;

Alternatively, $R_2$ and $R_3$ can be linked as shown in FIG. 4, so as to form an additional ring fused to the attached acridinium nucleus. The $C_1$, $C_2$, $C_3$, $C_4$, $C_5$, and $C_8$, peri-positions of the acridinium nucleus are optionally substituted as represented by $R_2'$.

Figure 5:
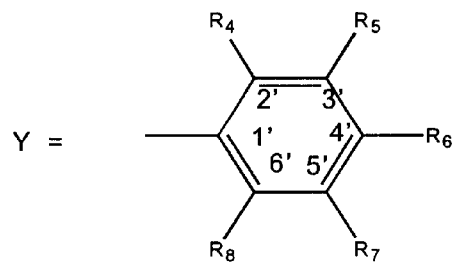
FIG. 5 shows the polysubstituted aryl moiety identified as Y.

$A^-$ is a counter ion which is introduced to pair with the quaternary nitrogen of the acridinium nucleus either as a result of quarternarizing the acridine ring nitrogen by the use of alkylating agents during the synthesis, modification of the $R_1$, or subsequent exchange that occurs during the work-up of reaction mixtures and purification of desired compounds in a solution or fluid containing excess amount of other anions. Examples of the counter ions include $CH_3SO_4^-$, $FSO_3^-$, $CF_3SO_3^-$, $C_4F_9SO_3^-$, $CH_3C_6H_4SO_3^-$, halide, $CF_3COO^-$, $CH_3COO^-$, and $NO_3^-$, X is nitrogen, oxygen or sulfur;

When X is oxygen or sulfur, Z is omitted and Y is a polysubstituted aryl moiety shown in FIG. 5, where $R_4$ and $R_8$ can be (1) hydrogen or (2) alkyl, alkenyl, alkynyl, alkoxyl (—OR), alkylthiol (—SR), or substituted amino groups that serve to stabilize the —COX— linkage between the acridinium nucleus and the Y moiety, through steric and/or electronic effects. Preferably, one of them is as defined below while the other is a hydrogen, if the $C_1$ or $C_8$ position of the acridinium nucleus is substituted with a lower alkyl group, preferably methyl. More preferably, $R_4$ and $R_8$ are alkyl, alkenyl, alkynyl, alkoxyl (—OR), alkylthiol (—SR), or substituted amino groups that serve to stabilize the —COX— linkage between the acridinium nucleus and the Y moiety, through steric and/or electronic effect. Most preferably $R_4$ and $R_8$ are lower alkyl (e.g., a methyl group).

$R_5$ and $R_7$ are any of $R_2$, $R_2'$, and $R_3$ defined above;

$R_6$ is also any of $R_2$, $R_2'$, and $R_3$ defined above, when the acridinium compound is used as a free chemiluminescent indicator.

Alternatively, the acridinium compounds can be covalently attached to a more water-soluble polymer (natural or synthetic) or biopolymers (e.g. proteins, polysaccharides, glycoproteins, and nucleic acids) in a conjugate form to enhance its water solubility for practical, commercial utility as chemiluminescent indicator. It will then be necessary to impart a reactive functional group, preferably, onto $R_6$ to facilitate covalent linkage formation between the acridinium compound and the water soluble polymer or biopolymer of choice.

Figure 6:
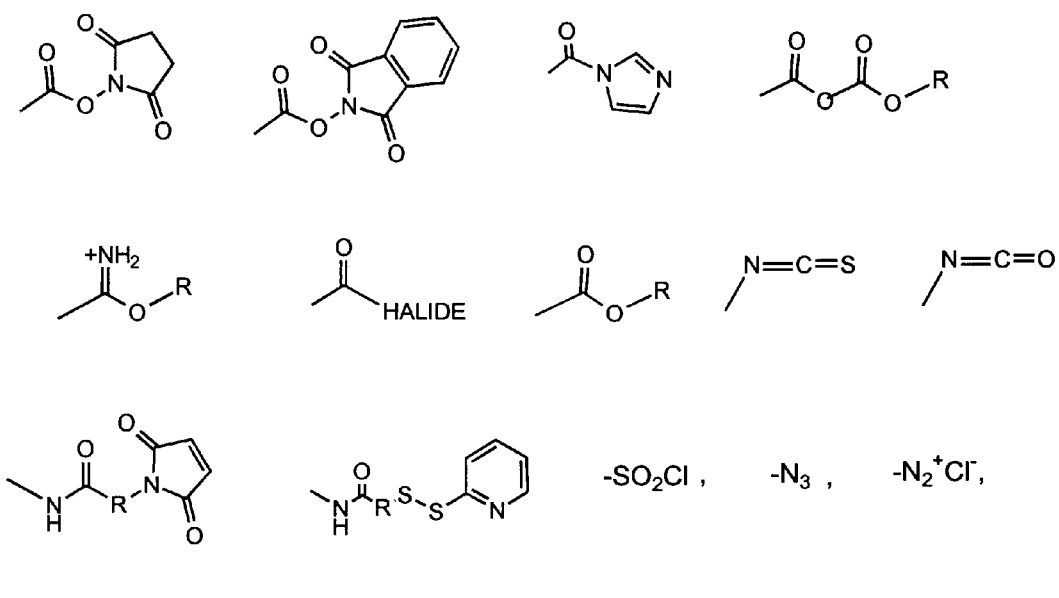
FIG. 6 shows examples of the leaving group $R_{10}$.

Thus, $R_6$ can also be $-R_9-R_{10}$, where $R_9$ is not required but optionally can be branched or straight-chained alkyl, substituted or unsubstituted aryl or aralkyl containing optionally up to 20 heteroatoms, and R10 is a leaving group or an electrophilic functional group attached with a leaving group including but not limited to those shown in FIG. 6. $R_{10}$ can also be —Q—R—Nu, —Q—R—(I)nNu—, —Q—Nu, —R—Nu, or —Nu, where n is a number of at least 1, Nu is a nucleophilic group, Q is a functional linkage, I is an ionic or ionizable group; detailed definitions of Nu, Q, and I can be found in the U.S. Pat. No. 5,241,070, column 3, line 45 to column 3, line 16. The reactions contemplated for Nu were also described in the same patent, column 3, line 48 to column 4, line 18.

$R_5$ and $R_6$, and $R_6$ and $R_7$ are interchangeable; and

When X is nitrogen, then Z is —$SO_2$—Y', Y' has the same definition of Y as described above, and both can be the same or different. Additionally, Y itself can be a branched or straight-chained alkyl containing optionally up to 20 carbon atoms, halogenated or unhalogenated, or a substituted aryl, or heterocyclic ring system.

Figure 7:
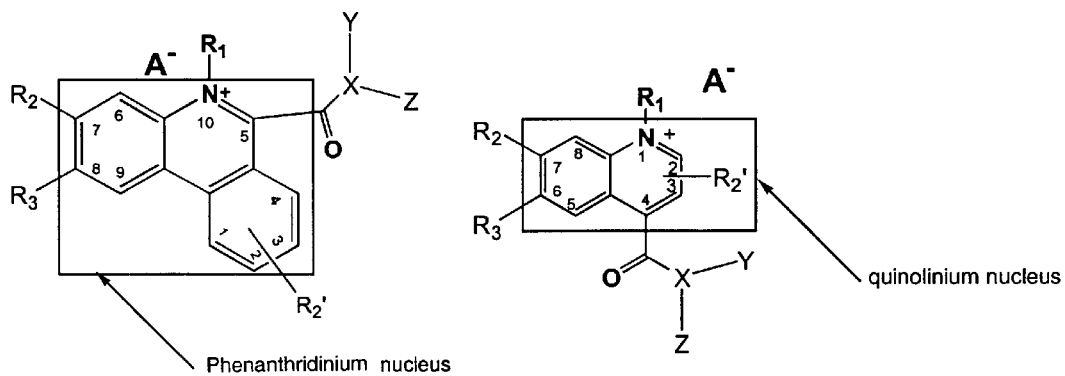
FIG. 7 shows the general structure of phenanthridinium and quinolinium compounds useful as the chemiluminescent indicators of the present invention.

Similarly, the general structure of the phenanthridinium and quinolinium compounds useful as the chemiluminescent indicators of the present invention can be schematically represented as shown in FIG. 7. All the definitions of the substituents and counter-ion of the phenanthridinium and quinolinium nucleus discussed above are the same as those described for the acridinium compounds earlier, except for the possible peri-positions for $R_2'$ substituent have to be re-designated at the $C_1$, $C_2$, $C_3$, $C_4$, $C_6$, and $C_9$ positions of the phenanthridinium nucleus and $C_2$, $C_3$, $C_5$, and $C_8$ positions of the quinolinium nucleus.

B. Alternative Modes of Hydride Modulation of Chemiluminescent Acridinium Compounds In addition to reduction of acridinium esters to acridans, hydride such as NADH can also be employed to modulate the chemiluminescent activity of acridinium compounds in other novel and interesting ways which can be potentially useful. Several such approaches are summarized below all of which require chemical selectivity (regioselectivity) in the reduction reaction.

1. Modulation of the Acridinium Ester or Sulfonylamide Cleavage Lability

Figure 8:
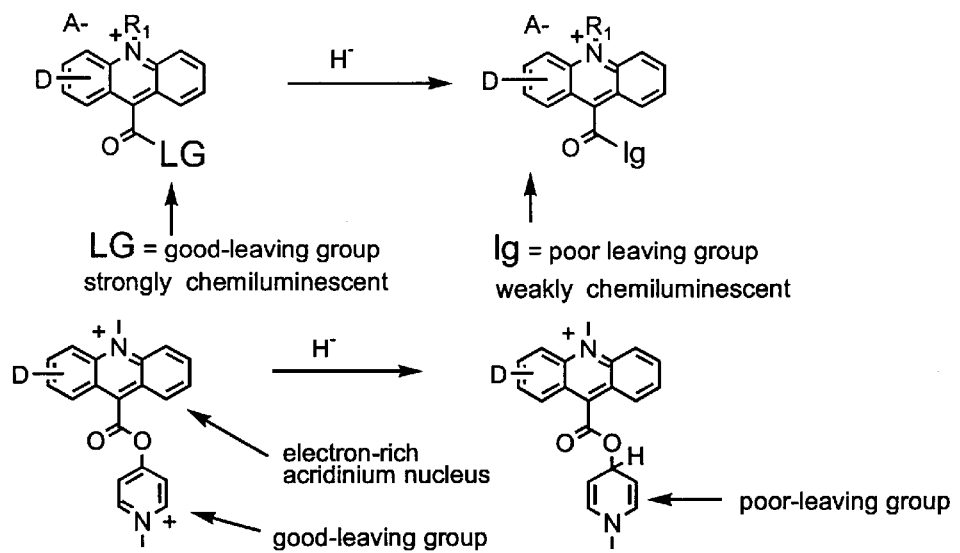
FIG. 8 shows the addition of a hydride to an electron-deficient ester moiety to form an electron-rich moiety.

In one approach, hydride can be directed to the ester or sulfonylamide moiety (instead of the acridinium nucleus) of the acridinium compound to effect a change in the emission characteristics of the compound. It is well known that acridinium esters with poor leaving groups are poorly chemiluminescent. Poor leaving groups are typically electron-rich and can be generated by hydride addition to electron-poor functional groups. By employing this procedure, an acridinium ester or sulfonylamide that contains an electron-deficient ester or sulfonylamide moiety can be converted to one which is electron-rich, thereby converting a strongly chemiluminescent compound to a weak one. FIG. 8 illustrates how this is achieved. While carrying some of the necessary basic substituents and the counter-ion as defined in section A above, the acridinium nucleus in the illustration is deliberately engineered to be electron-rich by the attachment of one or more desired electron-donating groups (relative to hydrogen and designated with letter D), which are as defined in "Advanced Organic Chemistry" Jerry March Ed., $4^{th}$ edition, page 18–19, at one or more optimal positions of the acridinium nucleus, so that reduction of the N-methylpyridinium moiety is achieved preferentially. If more than one electron-donating groups (D's) are substituted at the acridinium nucleus, the D's can be the same or different. To impart other important or desirable structural characteristics (e.g. hydrophilicity, functional group, etc.), other additional substituents are permissible at the peri-positions of the acridinium nucleus, as long as the combined electronic effect of all substituents is that of electron donating. Obviously, the same teaching applies to the analogs of the acridinium ester and sulfonylamide as described earlier in section A.

Figure 9:
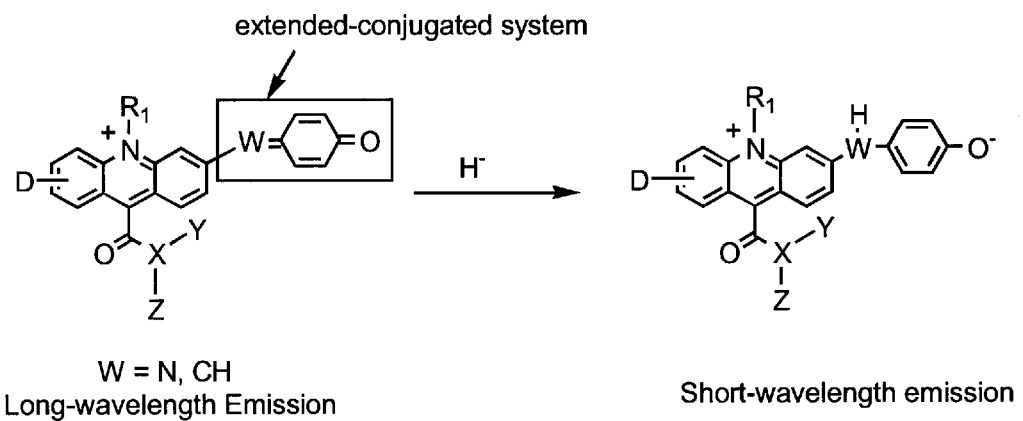
FIG. 9 shows the addition of hydride to a long-wavelength emission compound to form a short-wavelength emission compound.

2. Modulation of Emission Wavelength Maxima of Acridinium Compounds:

Reduction can also be used to alter the emission-wavelength of an acridinium compound. The emission-wavelength of blue-emitting acridinium compounds can be shifted to long wavelengths by creating an extended electronic conjugation system at the acridinium nucleus as discussed in PCT application PCT/US99/18076. By directing reduction to disrupt the extended conjugated system in an acridinium compound, emission wavelength of the acridinium compound can be shifted from long to short wavelength, hence varying the chemiluminescent intensity of the selected wavelength range under monitoring. FIG. 9 illustrates the above principle. Again, while carrying some of the necessary basic substituents and the counter-ion as defined in section A above, the acridinium nucleus in the illustration is also deliberately engineered to be electron-rich by the attachment of one or more desired electron-donating groups (relative to hydrogen and designated with letter D), at one or more optimal positions of the acridinium nucleus, so that reduction of the side chain extended conjugation system is achieved preferentially. If more than one electron-donating groups (D's) are substituted at the acridinium nucleus, the D's can be the same or different. To impart other important or desirable structural characteristics (e.g. hydrophilicity, functional group, etc.), other additional substituents are permissible at the peri-positions of the acridinium nucleus, as long as the combined electronic effect of all substituents is that of electron donating. Obviously, the same teaching applies to the analogs of the acridinium ester and sulfonylamide as described earlier in section A.

3. Modulation of Quencher/fluorophore Moiety of Acridinium Compounds:

Other modes of modulating the chemiluminescent activity are illustrated in the scheme in FIG. 9 where the hydride resulting from an enzymatic reaction alters the structure of the hydride-reducible quencher that is covalently linked to the acridinium moiety having group D, the purpose of which was described above, and thus alters the quenching effect. The prerequisite of the quencher here is its ability of quenching the chemiluminescent activity of the acridinium compound via dipole-dipole resonance energy transfer or other mechanisms, and its ability to be reduced by hydride preferentially over the reduction of the acridinium moiety. The reduction in quantum yield due to the quenching effect of the quencher can be reversed by the interaction of hydride with the quencher. Thus, in the presence of hydride, the quantum yield of the acridinium moiety of the conjugate will increase. One obvious advantage of modulating the chemiluminescent activity by hydride using acridinium-quencher conjugate is the positive correlation between the concentration of the hydride and chemiluminescent activity of the conjugate.

Figure 10:
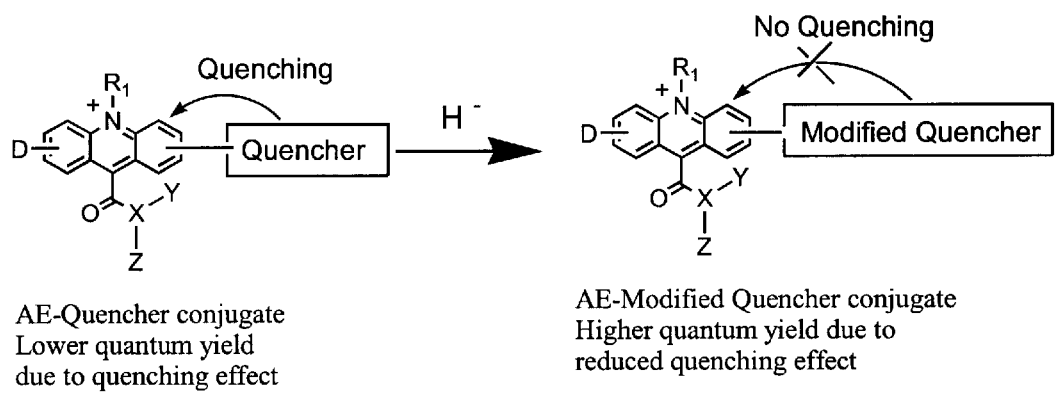
FIG. 10 shows an acridinium nucleus wherein the reduction of the side chain quencher is preferentially achieved.

Again, while carrying some of the necessary basic substituents and the counter-ion as defined in section A above, the acridinium nucleus in FIG. 10 can be attached with one or more desired electron-donating groups, D's at one or more optimal positions of the acridinium nucleus, so that reduction of the side chain quencher is achieved preferentially. If more than one electron-donating groups (D's) are substituted at the acridinium nucleus, the D's can be the same or different. Similarly, to impart other important or desirable structural characteristics (e.g. hydrophilicity, functional group, etc.), other additional substituents are permissible at the peri-positions of the acridinium nucleus, as long as the combined electronic effect of all substituents is that of electron donating. Obviously, the same teaching also applies to the analogs of the acridinium ester and sulfonylamide as described earlier in section A.

An alternative mode similar to the use of the acridinium compound-quencher conjugate is to replace the quencher with a fluorophore to form the AE-fluorophore conjugate. Acridinium-fluorophore conjugates, where the fluorophore is linked to the acridinium nucleus, in their chemiluminescent reactions, emit light in a region of the spectrum characteristic of the fluorophore. This occurs via resonance energy transfer from the electronically excited, acridone moiety to the fluorophore. The principle and examples of the AE-fluorophore conjugates are disclosed in more detail in PCT Application PCT/IB98/00831, which is incorporated herein by reference. One of the examples of this novel class of compounds is the conjugate of acridinium ester with rhodamine as shown below. The conjugate emits light at 628 nm due to efficient energy transfer from the AE moiety to rhodamine after it is treated with hydrogen peroxide in strong alkaline solution. The acridinium moiety can be modified by varying the D group so that the rhodamine moiety is selectively or preferentially reduced by hydride. As the result of the reduction, the light emission intensity at long wavelength due to the rhodamine moiety can decrease and the emission intensity at short wavelength due the acridinium moiety can increase. Thus, the quantitation of hydride is made possible either by detecting the decrease of the long emission signal or by detecting the increase of the short emission signal.

Figure 11:
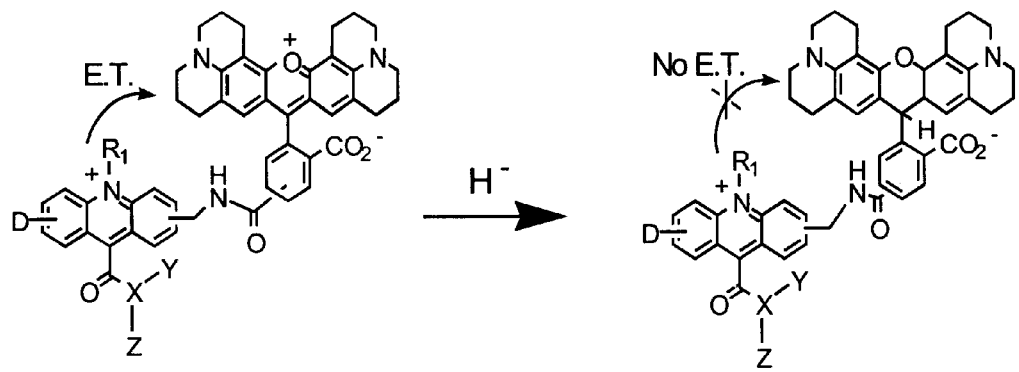
FIG. 11 shows an acridinium nucleus where reduction of the side chain fluorophore is preferentially achieved.

Again, while carrying some of the necessary basic substituents and counter-ions as defined in section A above, the acridinium nucleus in FIG. 11 can be attached with one or more desired electron-donating groups, D's at one or more optimal positions of the acridinium nucleus, so that reduction of the side chain fluorophore moiety is achieved preferentially. If more than one electron-donating groups (D's) are substituted at the acridinium nucleus, the D's can be the same or different. Similarly, to impart other important or desirable structural characteristics (e.g. hydrophilicity, functional group, etc.), other additional substituents are permissible at the peri-positions of the acridinium nucleus, as long as the combined electronic effect of all substituents is that of electron donating. Obviously, the same teaching also applies to the analogs of the acridinium ester and sulfonylamide as described earlier in section A.

C. Applications of the Chemiluminescent Indicators of Hydride

Figure 12:
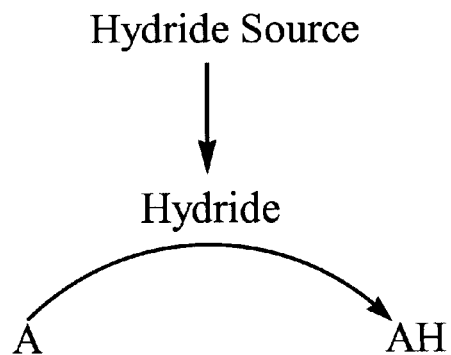
FIG. 12 shows an analytical procedure wherein NADH formation can be quantified.

1. Conversion of a Calorimetric to Chemiluminescent Emit® Assay:

Modulating the chemiluminescent activity of acridinium compounds with hydride has numerous applications in analytical measurements. As mentioned earlier, colored indicator molecules to monitor NADH formation have been used to devise sensitive immunoassays (see above). We have discovered that NADH (and by analogy any hydride) formation in a system can be quantified using acridinium ester (and by analogy any acridinium-type compound), the present invention discloses an analytical procedure as shown in FIG. 12. Here, A and AH represent oxidized and reduced forms of an acridinium compound whose chemiluminescent-emission properties are distinguishable. The hydride source can be chemical or biological. In addition, the hydride can be transferred either directly to the acridinium compound or indirectly through the intervention of an enzyme such as diaphorase.

One additional benefit of using the instant invention is that it allows a laboratory to measure hydride generation via the use of an instrument that measures chemiluminescence, thus eliminating the need to use a UV-visible spectrophotomer, which was needed in the past to measure hydride generation.

A widely used, commercial diagnostic test called Emit® (Emit® is a registered trademark of Behring Diagnostics GmBH and is defined below, Schneider, R. S. "Recent Advances in Enzyme Immunoassay" in Ligand Assay; Langan, J. and Clapp, J., Editors: Masson Publishing USA, Inc. 1981) employs a homogeneous immunoassay format and monitors and quantifies the formation of NADH (directly by UV spectrophotometry) whose concentration is correlated ultimately to the concentration of analyte. To demonstrate the utility of acridinium compounds as an excellent, quantitative indicator of NADH, we utilized this commercial test for three analytes (theophylline, quinidine and valproate) Similarly, an enzymatic assay for the determination of ethanol is also given in example 8 to demonstrate the utility of this approach. We also chose to employ the direct reduction of the acridinium compound with the NADH generated in the assay although it is obvious that this reduction can also be performed through the intervention of diaphorase.

The model chemiluminescent hydride indicators used for this study were 2',6'-dimethylphenyl-10-methyl-acridinium-9-carboxylate (DMAE-$\phi$) free label and 2',6'-dimethylphenyl-10-(3'-sulfopropyl)-acridinium-9-carboxylate(NSP-DMAE) conjugated via a carboxamide linkage to bovine serum albumin (BSA). A specific demonstration of the utility of acridinium esters as chemiluminescent redox indicators of hydride is described below where chemiluminescent signal from NSP-DMAE or DMAE-$\phi$ is used in an enzyme-immunoassay for the quantitation of theophylline, quinidine and valproate in serum and also in an enzymatic assay for the quantitation of ethanol in serum. For this purpose a prototype assay has been developed on the Bayer Diagnostics Corp. ACS:180® (ACS:180® is a registered trademark of Bayer Corporation for the Automated Chemiluminescence Analyzer: a fully automated immunodiagnostic assay system) using Behring Diagnostics Emit® 2000 Theophylline and Model 1 Valproate Assay reagents and also Bayer Corporation Immuno 1™ Emit® 2000 Quinidine Assay reagents as well as an enzymatic assay for the determination of ethanol in serum with the inclusion of an additional Chemiluminescent Redox Indicator reagent. DMAE-$\phi$ or NSP-DMAE-BSA conjugates are useful for applications in both organic and aqueous media. Since a broad variety of acridinium compounds which include the prior art hydrophilic AE's as described above have been well documented, the users of the present invention can select a highly water soluble acridinium compound to eliminate the use of organic solvents which are potentially detrimental to assay. Therefore, the user is provided with a number of options for selection of the chemiluminescent hydride indicator with appropriate solubility for application in an assay matrix with a given polarity.

Alternatively the acridinium compound selected as the chemiluminescent indicator for hydride might be conjugated to any number of small molecules, macromolecules or particulates, covalently or otherwise, to improve or impart properties such as, but not limited to, solubility, quantum yield, stability and resonance energy transfer.

Enzyme-multiplied immunoassay technique (Emit®) was originally developed by Syva Co., Inc. as a bioanalytical technology and is currently marketed in kits by Dade-Behring, Inc., chiefly for therapeutic drug monitoring (TDM) with some minor application for the detection of drugs of abuse. The automated, homogeneous Behring Diagnostics, Inc. Emit® assay series is currently one of several preferred diagnostics systems for TDM analytes. In these assays, a drug present in a patient sample will compete with a drug-enzyme conjugate for a limited quantity of antibody, directed against the drug. The conjugate's enzymatic activity, which in this case is that of the glucose-6-phosphate dehydrogenase (G6PDH) from *Leuconostoc mesenteroides*, is partially inhibited when bound to the drug-specific antibody. G6PDH catalyzes the reduction of oxidized nicotinamide adenine dinucleotide (NAD) to the reduced form, NADH, by hydride transfer from glucose-6-phosphate (G6P) and is monitored by the increased UV absorbance at 340 nm due to NADH formation. Endogenous sample G6PDH requires NADP, not NAD, for catalytic activity and will, therefore, not interfere with NAD reduction. Consequently, the G6PDH catalytic activity of the conjugate is correlated to the drug concentration in the patient sample through the rate of NADH formation, for example, $\Delta A_{340\ nm}$/minute. A Behring Diagnostics, Inc. Emit® assay kit holds two reagents: Reagent A contains a buffered solution of G6P (substrate), NAD (enzyme cofactor), and murine monoclonal antibodies reactive to a particular drug analyte, while Reagent B consists of a buffered solution of drug-G6PDH conjugate.

Since the Bayer Diagnostics ACS:180® readout system employs a photomultiplier tube to quantitate chemiluminescent signal, adaptation of a Behring Diagnostics, Inc. Emit® assay to the Bayer Diagnostics ACS:180® requires an additional reagent for transduction of the calorimetric signal to chemiluminescence. This additional reagent is termed a chemiluminescent redox indicator of hydride (CHI), and the CHI is an acridinium compound. The following experiments have indicated that several acridinium ester derivatives are reduced by hydride transfer (most likely to the C-9 position of the N-methylacridinium nucleus) from an equimolar concentration of NADH in the milli- and micromolar range. The rate of reduction is slow, most likely because the predominant pseudobase form is not susceptible to hydride reduction, ensuring that the differential decrease in chemiluminescence is observed even in the presence of a great excess of available hydride. For example, reduced DMAE-φ (N-alkylacridan) is weakly chemiluminescent, when compared to DMAE-φ, and yields little detectable signal when flashed; therefore, although the comparative concentration of NADH introduced into a mixture may be far greater than that of DMAE-φ, the relative NADH concentration is correlated to the decrease in total chemiluminescence. This correlation has been established. DMAE-φ, as well as NSP-DMAE, should, therefore, function as a chemiluminescent redox indicator of hydride in an Emit® type assay, where increased analyte concentrations would increase the rate of NADH formation, thereby decreasing the chemiluminescence of a fixed quantity of acridinium compound included within the assay reaction.

The ability to measure changes in NADH concentrations which are in the micro to millimolar range, with acridinium compounds or conjugates in the nanomolar range, has permitted us to measure changes in analyte concentrations (as reflected in changes in NADH concentrations) directly, without having to either dilute NADH containing samples or adding a secondary sink reagent to scavenge the vast excess of NADH in undiluted samples.

Figure 13:
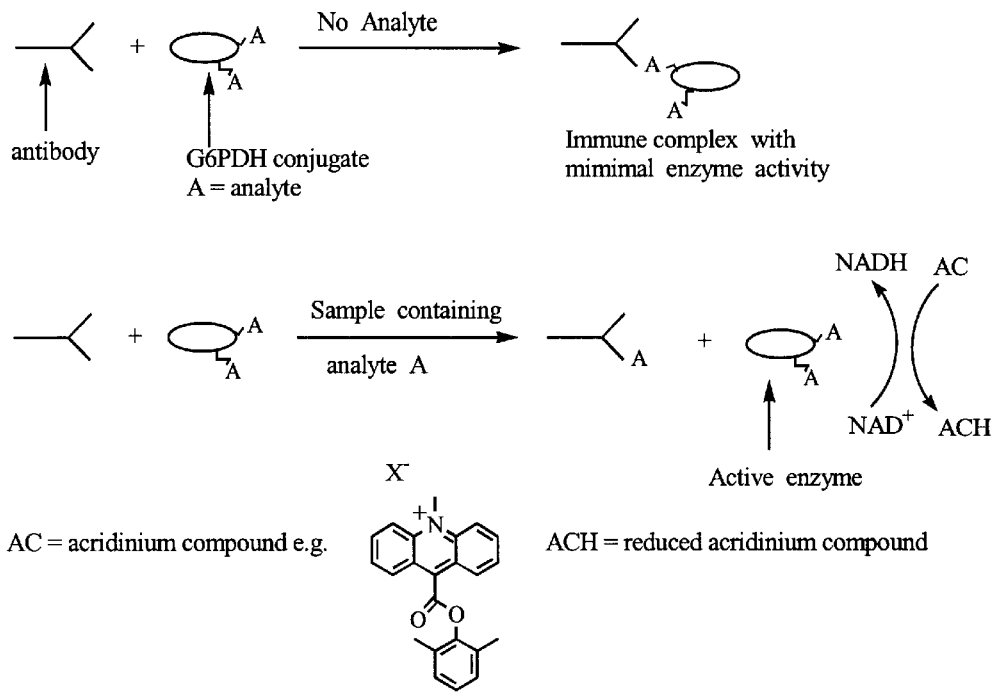
FIG. 13 shows a homogeneous immunoassay using an acridinium compound as a hydride indicator.

A schematic representation of the above assay is shown in FIG. 13 and examples of three analytes (theophylline, quinidine and valproate) measured using the aforementioned technique are described in detail in example 5–8 as well as for an enzymatic assay for the quantitation of ethanol. The data clearly indicate that acridinium compounds are indeed excellent, quantitative indicators of hydride.

Figure 14:
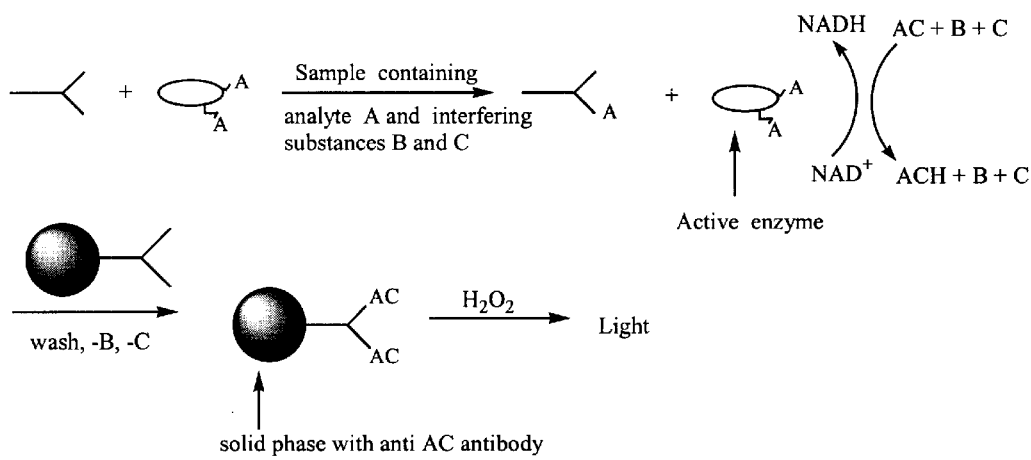
FIG. 14 shows an assay in which interfering substances are eliminated via the use of a solid phase in the assay.

3. Solving the Assay Interference From a Whole Blood Sample With the Insertion of a Solid Phase Capture Step:

The homogenous assay described above measures the residual chemiluminescent activity in the assay mixture i.e. increasing concentrations of analyte lead to decreasing levels of chemiluminescent activity remaining in the assay mixture. Since the assay is homogenous, extraneous substances in the sample e.g. from a whole blood sample, could potentially interfere or inhibit the chemiluminescent reaction of the acridinium compound with hydrogen peroxide. In the event this is observed, it is possible to manipulate the assay so that this interference/inhibition is removed. This can be accomplished in a most direct way as illustrated in FIG. 14. In this assay, a solid phase such as paramagnetic particles are introduced at the end of the homogenous assay. The particles are coated with an antibody which is specific for the acridinium compounds (Ref: U. Piran, et al., U.S. Pat. No. 5,445,936, "Method for Non-Competitive Binding Assays"). Following completion of the homogenous assay, the particles are introduced to capture the acridinium compound. The particles can then be washed to remove interfering substances prior to triggering the chemiluminescent reaction with hydrogen peroxide.

4. Heterogeneous Chemiluminescent Emit® Assays

Figure 15:
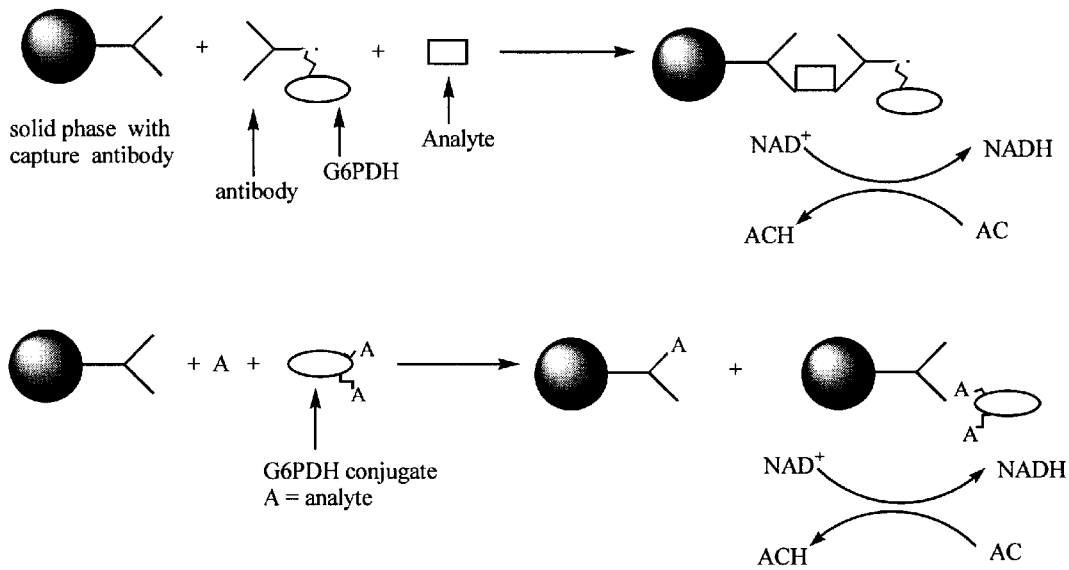
FIG. 15 illustrates heterogeneous assays using the instant invention.
Figure 16:
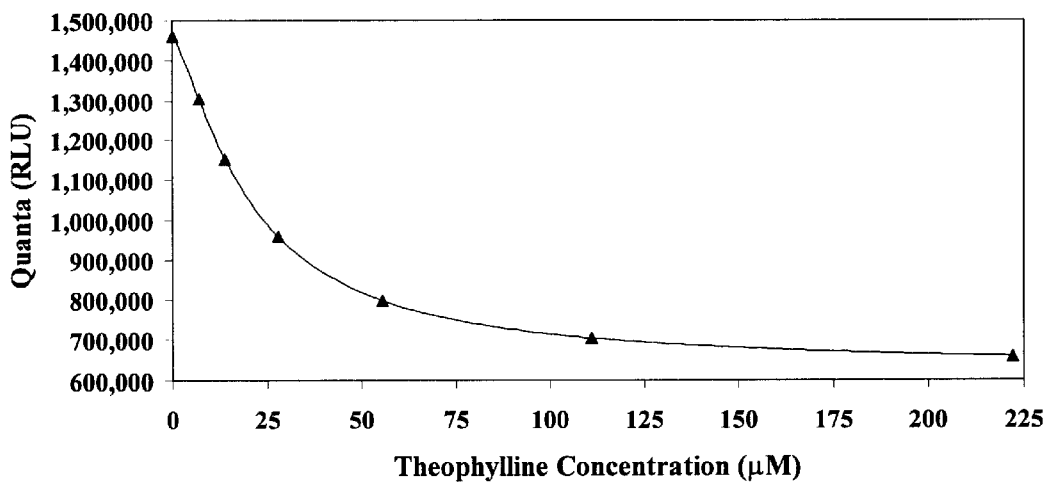
FIG. 16 shows the chemiluminometric Emit® theophylline assay using NSP-$DMAE_4$-BSA as a hydride indicator.
Figure 17:
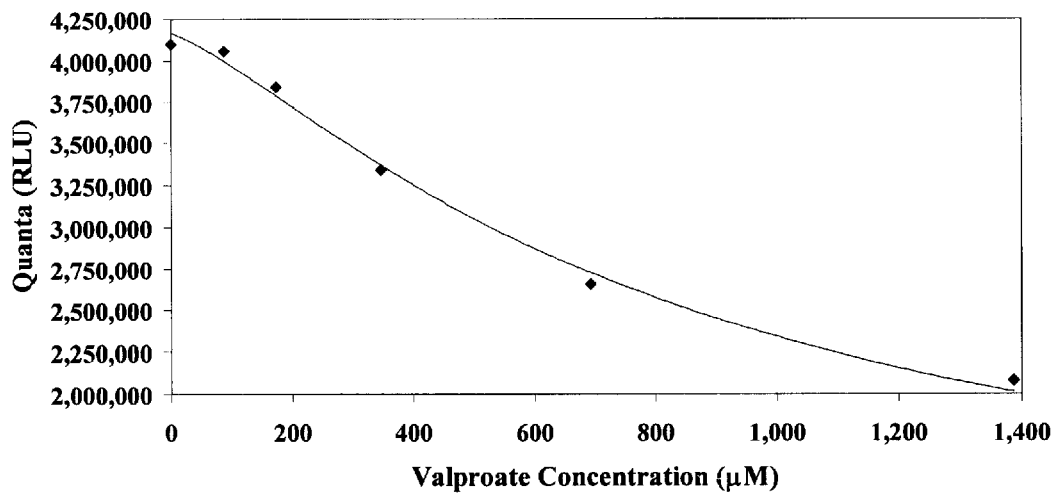
FIG. 17 shows the chemiluminometric Emit® valproate assay using NSP-$DMAE_4$-BSA as a hydride indicator.
Figure 18:
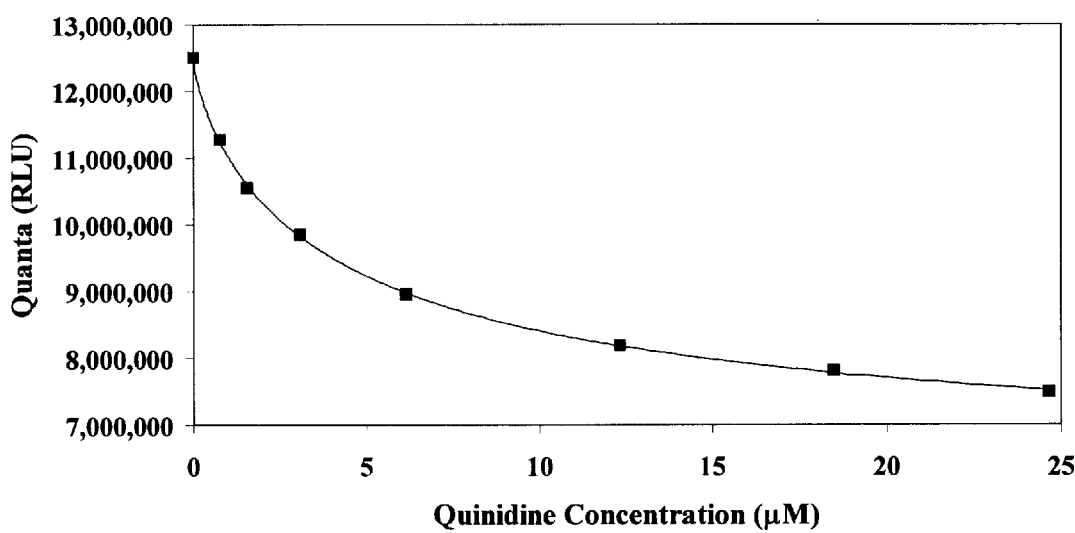
FIG. 18 shows the chemiluminometric Emit® quinidine assay using NSP-$DMAE_4$-BSA as a hydride indicator.
Figure 19:
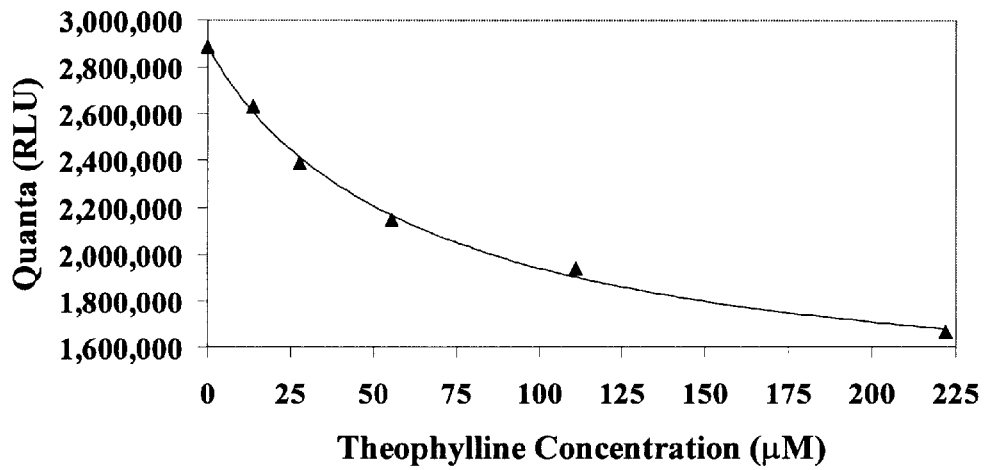
FIG. 19 shows the chemiluminometric Emit® theophylline assay using DMAE-φ as a hydride indicator.
Figure 20:
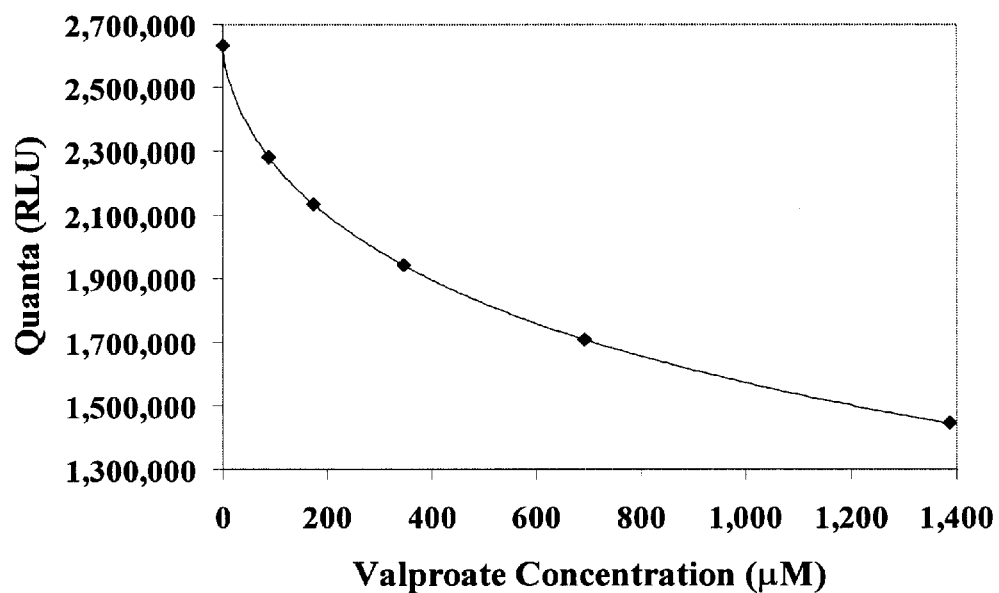
FIG. 20 shows the chemiluminometric Emit® valproate assay using DMAE-φ as a hydride indicator.

Assays that employ a heterogeneous format can also be coupled to the present invention. FIG. 15 illustrate how this may be performed. For a sandwich assay utilizing two antibodies, one of them can be coupled to the hydride generating system such as G6PDH, alcohol dehydrogenase etc. The concentration of the enzyme label in the assay is then measured by using the NADH generated by the enzyme to reduce the acridinium compound indicator molecule. Alternatively, in a competitive assay for a small analyte, the hydride generating system such as G6PDH can be coupled to the analyte for use in the assay as a tracer. Signal readout in the assay is accomplished in a similar manner as the sandwich assay.

It is also obvious that utilizing the hydride generating system such as the enzyme G6PDH as a label for nucleic acids will permit nucleic acid assays to be devised with acridinium compounds as the indicator of hydride.

Those with relevant expertise will recognize further variations which are consistent with the invention disclosed. This invention is illustrated but not limited, by the following examples.

EXAMPLE 1

2',6'-Dimethylcarbonylphenyl 10-Methylacridinium-9-Carboxylate Trifluoromethanesulfonate (DMAE-φ)

Synthesis of 2',6'-Dimethylphenyl Acridine-9-Carboxylate

Acridine-9-carboxylic acid (5 g) was refluxed with thionyl chloride (~25 mL) under a nitrogen atmosphere in an oil-bath. Reflux was maintained till the reaction turned clear. The solution was then cooled to room temperature and poured into benzene (200 mL, anhydrous). The benzene suspension was chilled in the refrigerator overnight to complete the precipitation of the acid chloride which was isolated by filtration and rinsed with anhydrous ether. Yield= 5.3 g (quant.)

The acid chloride (5.3 g) was mixed with 2,6-dimethylphenol, dimethylaminopyridine (0.5 g) in anhydrous pyridine (40 mL). The reaction was heated in an oil-bath at 100° C. for 3 hours. The reaction was then cooled to room temperature and the crude product was purified by flash chromatography on silica gel using 1:4, ethyl acetate in hexanes as eluent. Concentration of the flash fractions afforded the product as a bright yellow powder.

Synthesis of 2',6'-Dimethylphenyl 10-Methylacridinium-9-Carboxylate Trifluoromethanesulfonate A solution of 2',6'-dimethylphenyl acridine-9-carboxylate (20 mg, 0.061 mmol) in anhydrous dichloromethane (~2 mL) was treated with methyl trifluoromethanesulfonate (0.175 mL, 25 eq.). The reaction was stirred at room temperature. A yellow precipitate started forming in ~1 hour. The reaction was stirred for ~16 hours and then anhydrous ether (~50 mL) was added to precipitate the product which was collected by filtration and rinsed with ether and then air-dried. Yield=29 mg, MALDI-TOF MS 342.9 obs. (342.4 calc).

EXAMPLE 2

2',6'-Dimethylphenyl 10-methylacridan-9-carboxylate

Synthesis: A solution of 2',6'-dimethylphenyl-10-methylacridinium-9-carboxylate trifluoromethanesulfonate (50 mg, 0.105 mmol) in methanol (20 mL, partial solution) was cooled in an ice-bath and treated with sodium borohydride (20 mg, 0.525 mmol). The yellow color of the solution was bleached instantly. After 1 hour additional sodium borohydride (20 mg) was added and the reaction was warmed to room temperature and stirred for ~16 hours. The reaction was then quenched with acetic acid (1 mL) and evaporated to dryness. The residue was dissolved in acetonitrile. HPLC analysis on a 3.9×300 mm C18 column, with a 30-min. gradient of 10→>100% MeCN/water (0.05% TFA in each) at a flow rate of 1 mL/min. and UV-detection at 260 nm showed Rt=27 min (acridan), Rt=18 min (acridinium ester). The product was purified by preparative HPLC and the HPLC fractions were lyophilized to dryness to afford a white powder. Yield=30 mg (60%).

EXAMPLE 3

2',6'-Dimethylphenyl 10-(3'-Sulfopropyl)-acridinium-9-carboxyamidyl-BSA Conjugate Synthesis: Bovine serum albumin (1.65 mg, 25 nmol) was dissolved in 475 µL of 0.20 M $NaHCO_2$, pH 9.0. NSP-DMAE-NHS (U.S. Pat. No. 5,656,426) (0.61 mg, 1.03 µmol) was dissolved in 103 µL of N,N-dimethylformamide DMF to make a 10 mM solution. Twenty-five microliters of the 10 mM NSP-DMAE-NHS was mixed with the 475 µL of BSA solution and incubated at 4° C. for 16 hours. The conjugate was isolated in water by SEC. NSP-DMAE incorporation onto BSA was approximately four labels per protein molecule as calculated from the known chemiluminescent specific activity of the label and protein determination using the Bradford protein assay (6.4 µM).

EXAMPLE 4

Preparation of Chemiluminescent Hydride Indicator a. Nine milligrams (32 µmoles) of N(10)-methylacridinium tetrafluoroborate (NMA, Sigma-Aldrich) was dissolved in 320 µLs of N,N-dimethylformamide (DMF) to make a 0.10 M solution. A mass of 6.25 mgs (13 µmoles) of DMAE-φ was dissolved in 2.607 mLs of methanol, and was serially diluted in methanol to a concentration of 0.50 µM. Three hundred microliters of the 0.10 M NMA was mixed with 750 µLs of the 0.50 µM DMAE-φ into 1.95 mLs of water. Alternatively, NMA and two other hydride sinks, cetylpyridium chloride and crotonic acid, were dissolved in 0.20 M glycine buffer, 0.1% BgG, pH 7.4, when the chemiluminescent indicator of hydride used was a covalent conjugate of acridinium ester and IgG (Bayer Diagnostics). The acridinium ester-IgG conjugate was diluted to 12 nM in the same buffer.

b. Alternatively, NSP-DMAE$_4$-BSA conjugate was diluted to a concentration of 12 nM in a buffer of 0.20 M glycine, 1.0% (w/v) BSA, pH 7.4.

EXAMPLE 5

Theophylline Assay Using Acridinium Ester as a Chemiluminescent Indicator of Hydride In this automated, homogeneous enzyme-immunoassay, theophylline present in a patient sample will compete with a theophylline-G6PDH conjugate for binding to a limited quantity of anti-theophylline, murine, monoclonal antibody. Binding of the anti-theophylline antibody to the theophylline-G6PDH conjugate partially inhibits enzymatic activity. G6PDH catalyzes the reduction of oxidized nicotinamide adenine dinucleotide (NAD) to the reduced form NADH by hydride transfer from glucose-6-phosphate (G6P). Hydride is then chemically transferred from the NADH to DMAE-φ or NSP-DMAE conjugated to BSA. Consequently, the G6PDH catalytic activity of the conjugate is correlated to the theophylline concentration in the patient sample and inversely correlated to the residual chemiluminescence of the assay reaction.

The following assay was run in entirety by the Bayer Diagnostics ACS:180® (Bayer Diagnostics Corp., Walpole, Mass.). Cuvettes were loaded into the track, then 10 µLs of Bayer Diagnostics ACS Theophylline Assay standards or controls were added to their respective cuvettes in replicates of three. The standards contained theophylline in concentrations of 0.00, 13.9, 27.8, 55.5, 111 and 222 µM. The Bayer Diagnostics Ligand Controls 1, 2 and 3 contained theophylline in concentrations specified in the following table. To each cuvette, 300 µLs of Behring Diagnostics Emit® 2000 Theophylline Assay Reagent 1, containing a buffered solution of G6P, NAD, and anti-theophylline antibody, was added and incubated at 37° C. for 2 minutes and 40 seconds. To this was added 150 µLs Behring Diagnostics Emit® 2000 Theophylline Assay Reagent 2, consisting of a buffered solution of theophylline-G6PDH conjugate. The cuvettes were incubated at 37° C. for another 2 minutes and 40 seconds, then 20 µLs of the Chemiluminescent Indicator, containing either 10 mM NMA and 125 nM DMAE-φ in aqueous 10% (v/v) DMF and 25% (v/v) methanol or 12 nM NSP-DMAE$_4$-BSA conjugate, 0.20 M glycine, 1.0 % (w/v) BSA, pH 7.4, was added for a final incubation at 37° C. for 5 minutes. Since the assay is homogeneous Washes 1 and 2, as well as, Vacuums 1, 2 and 3 were switched off. The reaction mixtures were sequentially mixed with Bayer Diagnostics ACS Reagents 1 (0.1 N $HNO_3$, 0.5% (w/v) $H_2O_2$) and Reagent 2 (0.25 N NaOH, 0.5 % (w/v) N,N,N,N-hexadecyltrimethylammonium chloride surfactant) to initiate the chemiluminescent reaction.

EXAMPLE 6

Valproate Assay Using Acridinium Ester as a Chemiluminescent Indicator of Hydride In this automated, homogeneous enzyme-immunoassay, valproate present in a patient sample will compete with a valproate-G6PDH conjugate for binding to a limited quantity of anti-valproate, murine, monoclonal antibody. Binding of the anti-valproate antibody to the valproate-G6PDH conjugate partially inhibits enzymatic activity. G6PDH catalyzes the reduction of oxidized nicotinamide adenine dinucleotide (NAD) to the reduced form NADH by hydride transfer from glucose-6-phosphate (G6P). Hydride is then chemically transferred from the NADH to DMAE-φ or NSP-DMAE conjugated to BSA. Consequently, the G6PDH catalytic activity of the conjugate is correlated to the valproate concentration in the patient sample and inversely correlated to the residual chemiluminescence of the assay reaction.

The following assay was run in entirety by the Bayer Diagnostics ACS:180® (Bayer Diagnostics Corp., Walpole, Mass.). Cuvettes were loaded into the track, then 10 µLs of Bayer Diagnostics in-house ACS Valproate Assay standards or controls were added to their respective cuvettes in replicates of three. The standards contained valproate in concentrations of 0.000, 86.7, 173, 347, 693 and 1387 µM. The Bayer Diagnostics in-house TDM Controls A, B and C contained valproate in concentrations specified in the following table. To each cuvette, 225 µLs of Behring Diagnostics Emit® Model 1 Valproate Assay Reagent A, containing a buffered solution of G6P, NAD, and anti-valproate antibody, was added and incubated at 37° C. for 2 minutes and 40 seconds. To this was added 225 µLs Behring Diagnostics Emit® Model 1 Valproate Assay Reagent B, consisting of a buffered solution of valproate-G6PDH conjugate. The cuvettes were incubated at 37° C. for another 2 minutes and 40 seconds, then 20 µLs of the Chemiluminescent Indicator, containing either 10 mM NMA and 125 nM DMAE-φ in aqueous 10% (v/v) DMF and 25% (v/v) methanol or 12 nM NSP-DMAE$_4$-BSA conjugate, 0.20 M glycine, 1.0% (w/v) BSA, pH 7.4, was added for a final incubation at 37° C. for 5 minutes. Since the assay is homogeneous Washes 1 and 2, as well as, Vacuums 1, 2 and 3 were switched off. The reaction mixtures were sequentially mixed with Bayer Diagnostics ACS Reagents 1 (0.1 N HNO$_3$, 0.5% (w/v) H$_2$O$_2$) and Reagent 2 (0.25 N NaOH, 0.5 µ(w/v) N,N,N,N-hexadecyltrimethylammonium chloride surfactant) to initiate the chemiluminescent reaction. Chemiluminescence data were collected for five seconds as photons detected by ACS luminometer and expressed in relative light units (RLUs).

EXAMPLE 7

Quinidine Assay Using Acridinium Ester as a Chemiluminescent Indicator of Hydride In this automated, homogeneous enzyme-immunoassay, quinidine present in a patient sample will compete with a quinidine-G6PDH conjugate for binding to a limited quantity of anti-quinidine, murine, monoclonal antibody. Binding of the anti-quinidine antibody to the quinidine-G6PDH conjugate partially inhibits enzymatic activity. G6PDH catalyzes the reduction of oxidized nicotinamide adenine dinucleotide (NAD) to the reduced form NADH by hydride transfer from glucose-6-phosphate (G6P). Hydride is then chemically transferred from the NADH to NSP-DMAE conjugated to BSA. Consequently, the G6PDH catalytic activity of the conjugate is correlated to the quinidine concentration in the patient sample and inversely correlated to the residual chemiluminescence of the assay reaction.

The following assay was run in entirety by the Bayer Diagnostics ACS:180® (Bayer Diagnostics Corp., Walpole, Mass.). Cuvettes were loaded into the track, then 10 µLs of Bayer Diagnostics in-house ACS Quinidine Assay standards were added to their respective cuvettes in replicates of three. The standards contained quinidine in concentrations of 0.00, 0.77, 1.5, 3.1, 6.2, 12, 18 and 25 µM. To each cuvette, 160 µLs of Bayer Corporation Emit® 2000 Quinidine Assay Reagent A, containing a buffered solution of G6P, NAD, and anti-quinidine antibody, was added and incubated at 37° C. for 2 minutes and 40 seconds. To this was added 80 µLs Bayer Corporation Emit® 2000 Quinidine Assay Reagent B, consisting of a buffered solution of quinidine-G6PDH conjugate. The cuvettes were incubated at 37° C. for another 2 minutes and 40 seconds, then 20 µLs of the Chemiluminescent Indicator, containing 12 nM NSP-DMAE$_4$-BSA conjugate, 0.20 M glycine, 1.0% (w/v) BSA, pH 7.4, was added for a final incubation at 37° C. for 5 minutes. Since the assay is homogeneous Washes 1 and 2, as well as, Vacuums 1, 2 and 3 were switched off. The reaction mixtures were sequentially mixed with Bayer Diagnostics ACS Reagents 1 (0.1 N HNO$_3$, 0.5% (w/v) H$_2$O$_2$) and Reagent 2 (0.25 N NaOH, 0.5% (w/v) N,N,N,N-hexadecyltrimethylammonium chloride surfactant) to initiate the chemiluminescent reaction. Chemiluminescence data were collected for five seconds as photons detected by ACS luminometer and expressed in relative light units (RLUs).

EXAMPLE 8

Homogeneous, Chemiluminometric, Enzyme Assay for Ethanol Using Acridinium Ester as a Chemiluminescent Indicator of Hydride In this automated, homogeneous enzyme assay, ethanol from the patient sample is oxidized to acetaldehyde through the specific catalytic action of a fixed quantity of yeast alcohol dehydrogenase (ADH) with concurrent hydride reduction of the cofactor nicotinamide adenine dinucleotide (NAD) to NADH. Equilibrium in favor of oxidation of ethanol to acetaldehyde is further promoted with the addition of a hydrazide aldehyde scavenger. Hydride is chemically transferred from the NADH to NSP-DMAE conjugated to BSA. Consequently, the ethanol concentration is correlated to NADH formation and inversely related to the residual chemiluminescence of the assay reaction.

The following assay was run in entirety by the Bayer Diagnostics ACS:180® (Bayer Diagnostics Corp., Walpole, Mass.). Cuvettes were loaded into the track, then 10 µLs of standards prepared by serial dilution of ethanol in serum were added to their respective cuvettes in replicates of three. The standards contained ethanol in concentrations of 0.00, 0.025, 0.050, 0.10, 0.20, and 0.40% (w/v) To each cuvette, 150 µLs of Ethanol Assay Reagent A, containing 0.15 M sodium phosphate, 0.15 M hydrazinecarboxamide hydrochloride, pH 9.0, was added and incubated at 37° C. for 2 minutes and 40 seconds. To this was added 150 µLs Ethanol Assay Reagent B, consisting of 22 mM glycine, 12 mM NAD, 14 µM ADH, 1.0 mg/mL BSA, pH7.0. The cuvettes were incubated at 37° C. for another 2 minutes and 40 seconds, then 20 µLs of the Chemiluminescent Indicator, containing 12 nM NSP-DMAE$_4$-BSA conjugate, 0.20 M glycine, 1.0% (w/v) BSA, pH 7.4, was added for a final incubation at 37° C. for 5 minutes. Since the assay is homogeneous Washes 1 and 2, as well as, Vacuums 1, 2 and 3 were switched off. The reaction mixtures were sequentially mixed with Bayer Diagnostics ACS Reagents 1 (0.1 N HNO$_3$, 0.5% (w/v) H$_2$O$_2$) and Reagent 2 (0.25 N NaOH, 0.5% (w/v) N,N,N,N-hexadecyltrimethylammonium chloride surfactant) to initiate the chemiluminescent reaction. Chemiluminescence data were collected for five seconds as photons detected by ACS luminometer and expressed in relative light units (RLUs).

Method of Calculation for Assay Parameters. Arithmetic means for RLUs resulting from a specific analyte concentration, represented here as µ, were calculated from three replicates. An inverse, non-linear relationship exists between the analyte concentration present in the standard and the detected RLUs, $$y = y_0 + \frac{(y_\infty - y_0)}{(1 + 10^{-m\log x - b})}$$

where x is the analyte concentration, and y is the observed signal generated as RLUs (Rodbard, David; *Ligand Analysis*; (1981); Langon, J.; Clapp, J. (Eds.); Masson Publishing, Inc., New York; pp. 45–101) (Nix, Barry; *The Immunoassay Handbook*; (1994); Wild, David (Ed.); Stockton Press, Inc., New York; pp. 117–123) (Van Lente, Frederick, Galen, Robert S.; *Enzyme-immunoassay*; (1980); Maggio, Edward T. (Ed.); CRC Press, Inc., Boca Raton; pp. 135–153).

Additionally, there are four parameters, namely the regression constant, b, the regression coefficient, m, the asymptotic limit at infinite dose, $y_\infty$, and the asymptotic limit for the zero dose, $y_0$. The latter three of these parameters were calculated directly using the iterative, standard, four-parameter logistic (4PL-STD) analysis function of the DOSECALC.EXE Rev.1.73 program (Bayer Diagnostics Corp., Walpole, Mass.). The arithmetic mean of the regression constant b was determined over the entire range of analyte concentrations as calculated from the dose response expression re-written as $$b = -\log\frac{y_\infty - y}{y - y_0} - m\log x.$$

Analyte concentrations of unknowns were subsequently calculated using the dose response equation arranged as $$x = 10^{\frac{\log[(y_\infty - y)/(y - y_0)] + b}{-m}}.$$

Theophylline, Quinidine and Valproate Assay Standard Curves Using Acridinium Ester as a Chemiluminescent Indicator of Hydride. A plot of the RLUs versus analyte concentration illustrates the inverse, non-linear relationship between chemiluminescence and analyte concentration. Precision was good, being under 5% C.V. for all points.

Clearly, acridinium compounds will function as chemiluminescent indicators of hydride either as free indicators dissolved in organic solvent or as hydrophilic conjugates when covalently linked to protein.

Figures 21, 22:
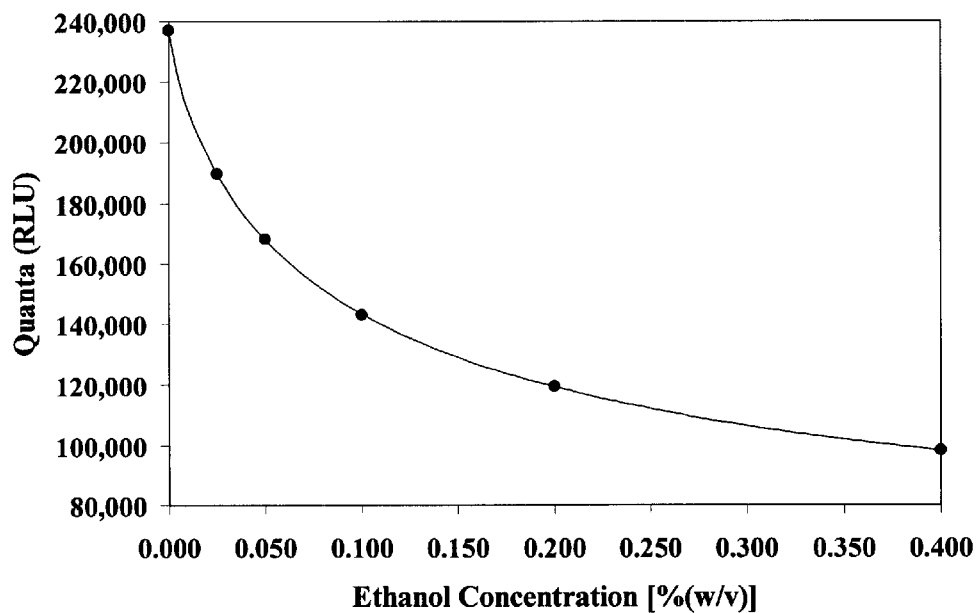
FIG. 21 shows referenced vs. determined analyte concentration for controls.
FIG. 22 shows a chemiluminometric ethanol assay.

Assay Accuracy in Determination of Theophylline and Valproate Concentrations. Analyte concentrations were determined for the Ligand Controls using the standard 4PL function. The determined values were compared to the established ranges stated in the associated product literature, as shown in FIG. 21.

Variation in specified analyte ranges between different assay constructs is considerable for a number of multi-level ligand controls because of the different susceptibility to the matrix effect. Since acceptable ranges of analyte concentrations have not yet been established for the new assay format described in the present invention, some difference is expected. Determined values are similar enough to referenced control limits that we can demonstrate the utility of an acridinium compound as a chemiluminescent indicator of hydride for the quantitation of theophylline and valproate in a homogeneous, enzyme-immunoassay.

EXAMPLE 9

Ethanol Assay Standard Curves Using Acridinium Ester as a Chemiluminescent Indicator of Hydride.

A plot of the RLUs versus analyte concentration (see FIG. 22) illustrates the inverse, non-linear relationship between chemiluminescence and analyte concentration. As with the chemiluminometric Emit® assays precision in the ethanol assay was good being under 5% C.V. for all points.

We claim:

1. A method for determining the amount of hydride produced in a reaction mixture wherein hydride is generated comprising (a) adding a known amount of a chemiluminescent compound to said reaction mixture, (b) adding reagents to said reaction mixture in step (a) wherein said reagents cause the release of chemiluminescence from said chemiluminescent compound, (c) measuring the amount of chemiluminescence given off from said reaction mixture after the addition of said reagents which release chemiluminescence, (d) comparing (1) the amount of chemiluminescence produced with (2) the expected chemiluminescence in the absence of said hydride to determine the difference in amount of chemiluminescence between (d)(1) and (d)(2), and (e) calculating the amount of said hydride present by comparison of said difference in chemiluminescence with a standard curve, wherein said measuring the amount of chemiluminescence in step (c) does not involve the use of peroxidase and wherein no hydrogen peroxide is produced in said method.

2. The method of claim 1 wherein said reaction mixture further comprises a patient sample.

3. The method of claim 2 in which said hydride reacts with the nucleus of said chemiluminescent compound.

4. The method of claim 2 in which said hydride reacts with the conjugate of said chemiluminescent compound.

5. The method of claim 2 in which said hydride reacts with the ester or sulfonylamide derivative of said chemiluminescent compound.

6. The method of claim 2 in which said hydride reacts with said chemiluminescent compound containing (a) an extended electronic conjugation system, (b) a hydride-reducible quencher, (c) one or more electron donating groups, or (d) a fluorescent resonance energy acceptor.

7. The method of claim 2 wherein said hydride is produced in said reaction mixture wherein an assay for an analyte is conducted.

8. The method of claim 2 in which said chemiluminescent compound is an acridinium, benzacridinium, phenanthridinium, quinolinium or lucigenin compound, or the conjugate of said acridinium, benzacridinium, phenanthridinium, quinolinium or lucigenin compound.

9. The method of claim 8 in which said acridinium or benzacridinium compound is an acridinium ester or benzacridinium ester, acridinium sulfonylamide or benzacridinium sulfonylamide.

10. The method of claim 2 in which said hydride is produced in a biochemical redox reaction of an enzyme cofactor.

11. The method of claim 10 in which said cofactor is nicotinamide adenine dinucleotide, nicotinamide adenine dinucleotide phosphate, flavin mononucleotide and flavin adenine dinucleotide.

12. The method of claim 2 wherein said hydride is generated from said reaction mixture wherein the amount of an analyte is determined.

13. The method of claim 12 in which said analyte is theophylline, valproate, quinidine or ethanol and said patient sample is serum.

14. The method of claim 8 wherein said chemiluminescent compound is a hydride indicator having the structure

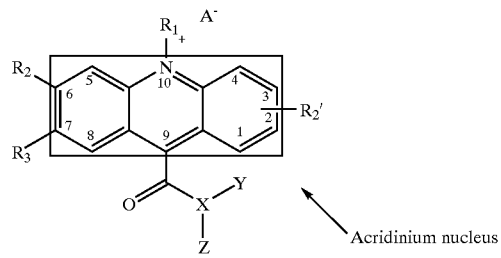

Acridinium nucleus wherein $R_1$, is an alkyl, alkenyl, alkynyl or aralkyl containing optionally up to 20 heteroatoms; preferably $R_1$ is methyl or sulfoalkyl group;

$R_2$, $R_2'$, and $R_3$, are identical or different, selected from hydrogen, —R, substituted or unsubstituted aryl, wherein said substituent is selected from the group consisting of halide, amino, hydroxyl, nitro, sulfonate, —CN, —COOH, —SCN, —OR, —SR, —SSR, —C(O)R, —C(O)OR, —C(O)NHR, and —NHC(O)R;

R is selected from the group consisting of alkyl, alkenyl, alkynyl, aryl, and aralkyl containing optionally up to 20 heteroatoms;

alternatively, $R_2$ and $R_3$ can be linked so as to form an additional ring fused to the attached acridinium nucleus;

$C_1, C_2, C_3, C_4, C_5$, and $C_8$, peri-positions of the acridhium nucleus are optionally substituted as represented by $R_2'$, $A^-$ is a counter ion which is introduced to pair with the quarternery nitrogen of the acridinium nucleus either as a result of quarternerizing the acridine ring nitrogen by the use of alkylating agents during the synthesis, modification of the $R_1$, or subsequent exchange that occurs during the work-up of reaction mixtures and purification of desired compounds in a solution or fluid containing excess amount of other anions;

X is nitrogen, oxygen or sulfur; such that, when X is oxygen or sulfur, Z is omitted and Y is a polysubstituted aryl moiety;

$R_5$ and $R_7$ are any of $R_2, R_2'$, and $R_3$ defined above;

$R_6$ is also any of $R_2, R_2'$, and $R_3$ defined above, when the acridinium compound is used as a free chemiluminescent indicator, said acridinium compounds being optionally covalently attached to a water-soluble polymer or biopolymers in a conjugate form for enhanced water solubility;

$R_5$ and $R_6$, and $R_6$ and $R_7$ are interchangeable; such that when X is nitrogen, then Z is —$SO_2$—Y', Y' being defined as Y above, and both can be the same or different, with Y optionally being a branched or straight-chained alkyl containing up to 20 carbon atoms, or a substituted aryl, or heterocyclic ring system.

15. The method of claim 14 wherein said counter ion of said chemiluminescent compound is selected from the group consisting of $CH_3SO_4^-$, $FSO_3^-$, $CF_3SO_3^-$, $C_4F_9SO_3^-$, $CH_3C_6H_4SO_3^-$, halide, $CF_3COO^-$, $CH_3COO^-$, and $NO_3^-$;

said polysubstituted aryl moiety is

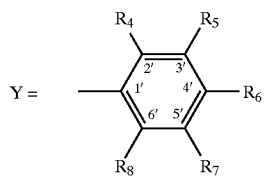

where $R_4$ and $R_8$ are selected from the group consisting of hydrogen, alkyl, alkenyl, alkynyl, alkoxyl, alkylthiol, substituted amino groups that serve to stabilize the —COX— linkage between the acridlnium nucleus and the Y moiety, through steric or electronic effects;

$R_6$ can also be —$R_9$–$R_{10}$, where $R_9$ is not required but optionally can be branched or straight-chained alkyl, substituted or unsubstituted aryl or aralkyl containing optionally up to 20 heteroatoms, and $R_{10}$ is a leaving group or an electrophilic functional group attached with a leaving group having the structure

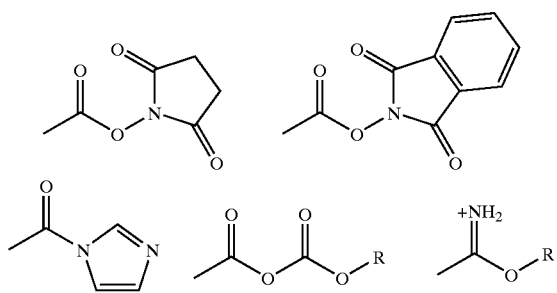

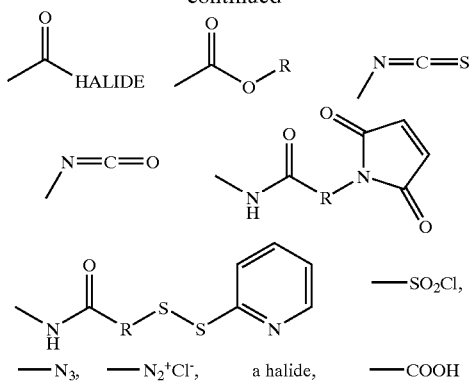

$R_{10}$ can also be —Q—R—Nu, —Q—R—(I)nNu—, —Q—Nu, —R—Nu, or —Nu, where n is a number of at least 1, Nu is a nucleophilic group, Q is a functional linkage, I is an ionic or ionizable group.

16. The method of claim 14 wherein said indicator is a phenanthridinium or quinolinium compound having the structure

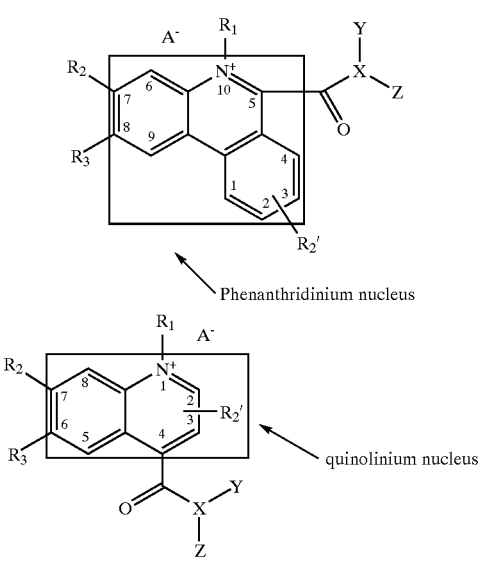

with substituents being the same as in claim 14, except that the peri-positions for $R_2'$ substituent are re-designated at the $C_1, C_2, C_3, C_4, C_6$, and $C_9$ positions of said phenanthridinium nucleus and $C_2, C_3, C_5$, and $C_8$ positions of said quinolinium nucleus.

17. The method of claim 12, wherein said patient sample is whole blood, said chemiluminescent compound is an acridinium compound and said method comprises (a) adding sequentially to said whole blood sample, colorimetric assay reagents for hydride and a chemiluminescent acridinium compound which can react with hydride, (b) adding a solid phase coated with an antibody which can bind said acridinium compound, (c) separating said solid phase with said captured acridinium compound from said whole blood sample, (d) adding alkaline peroxide or peroxide salt to said solid phase in (c) to trigger chemiluminescence of said acridinium compound captured by said solid phase, and (e) comparing the chemiluminescence from (d) with a calibration curve to determine the amount of analyte in said whole blood sample.

18. The method of claim 2, wherein said patient sample is whole blood, said chemiluminescent compound is an acridinium compound and said method comprises (a) adding sequentially to said whole blood sample, colorimetric assay reagents for hydride and a chemiluminescent acridinium compound which can react with hydride, (b) adding a solid phase coated with an antibody which can bind said acridinium compound, (c) separating said solid phase with said captured acridinium compound from said whole blood sample, (d) adding alkaline peroxide or peroxide salt to said solid phase in (c) to trigger chemiluminescence of said acridinium compound captured by said solid phase, and (e) comparing the chemiluminescence from (d) with a calibration curve to determine the amount of hydride present in said whole blood sample.

19. The method of claim 1 wherein said chemiluminescent compound and said reagents which release said chemiluminescence are contained within a kit.

20. The method of claim 7 wherein said assay is selected from the group consisting of homogeneous or heterogeneous immunoassays, nucleic acid assays, and enzyme assays.

21. The method of claim 15 wherein, when $C_1$ or $C_8$ is substituted with a lower alkyl group, either $R_4$ or $R_8$ is a hydrogen.

22. The method of claim 7 wherein said assay is a protein assay.

23. The method of claim 1 wherein said reagents in step (b) that cause the release of chemiluminescence are alkaline hydrogen peroxide or peroxide salts.

24. A method for determining the amount of hydride produced in a sample wherein hydride is generated, said method comprising (a) adding a known amount of a chemiluminescent compound to said sample, (b) adding reagents to said sample in step (a) which cause the release of chemiluminescence from said chemiluminescent compound, (c) measuring the amount of chemiluminescence given off from said sample after the addition of said reagents which release chemiluminescence, (d) comparing (1) the amount of chemiluminescence produced with (2) the expected chemiluminescence in the absence of said hydride to determine the difference in amount of chemiluminescence between (d)(1) and (d) (2), and (e) calculating the amount of said hydride present by comparison of said difference in chemiluminescence with a standard curve, wherein said measuring the amount of chemiluminescence in step (c) does not involve the use of peroxidase and wherein no hydrogen peroxide is produced in said method.

* * * * *

UNITED STATES PATENT AND TRADEMARK OFFICE
CERTIFICATE OF CORRECTION

PATENT NO. : 6,673,560 B1
DATED : January 6, 2004
INVENTOR(S) : David Sharpe et al.

It is certified that error appears in the above-identified patent and that said Letters Patent is hereby corrected as shown below:

Column 1,
Line 37, "$\mu$Sons," should read -- & Sons, --;

Column 2,
Line 41, "$\mu$Sons," should read -- & Sons, --;

Column 1,
Line 14, "$\mu$ (w/v)" should read -- % (w/v) --; and

Column 19,
Line 47, "acridlnium" should read -- acridinium --.

Signed and Sealed this

Third Day of May, 2005

JON W. DUDAS
*Director of the United States Patent and Trademark Office*

UNITED STATES PATENT AND TRADEMARK OFFICE
CERTIFICATE OF CORRECTION

PATENT NO. : 6,673,560 B1
DATED : January 6, 2004
INVENTOR(S) : David Sharpe et al.

It is certified that error appears in the above-identified patent and that said Letters Patent is hereby corrected as shown below:

Column 1,
Line 37, "$\mu$Sons," should read -- & Sons, --;

Column 2,
Line 41, "$\mu$Sons," should read -- & Sons, --;

Column 15,
Line 14, "$\mu$ (w/v)" should read -- % (w/v) --; and

Column 19,
Line 47, "acridlnium" should read -- acridinium --.

This certificate supersedes Certificate of Correction issued May 3, 2005.

Signed and Sealed this

Twenty-third Day of August, 2005

JON W. DUDAS
*Director of the United States Patent and Trademark Office*